United States Patent
Tang et al.

(10) Patent No.: US 6,221,843 B1
(45) Date of Patent: Apr. 24, 2001

(54) HUMAN KERATINS

(75) Inventors: Y. Tom Tang, San Jose; Jennifer L. Hillman; Neil C. Corley, both of Mountain View; Mariah Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/360,490

(22) Filed: Jul. 23, 1999

Related U.S. Application Data

(62) Division of application No. 09/067,351, filed on Apr. 27, 1998, now Pat. No. 5,994,081.

(51) Int. Cl.$^7$ .............................. A61K 38/00; C07K 1/00; G01N 33/00
(52) U.S. Cl. ................................ 514/12; 436/86; 530/350
(58) Field of Search .............................. 530/350; 514/12; 436/86

(56) References Cited

PUBLICATIONS

Lodish, H. et al., *Molecular Cell Biology*, Scientific American Books, New York, NY, pp. 1106–1116 (1995).

Fuchs, E. and D.W. Cleveland, "A Structural Scaffolding of Intermediate Filaments in Health and Disease", *Science*, 279: 514–519 (1998).

Fuchs, E., "Of Mice and Men: Genetic Disorders of the Cytoskeleton", *Mol. Biol. Cell*, 8: 189–203 (1997).

Takahashi, K. et al., "Cloning and Characterization of Multiple Human Genes and cDNAs Encoding Highly Related Type II Keratin 6 Isoforms", *J. Biol Chem.*, 270: 18581–18592 (1995).

Takahashi, K. et al., (Direct Submission), GenBank Sequence Database (Accession L42475), National Center for Biotechnology Information, National Library Medicine, Bethesda, Maryland, 20894, (GI 908769; GI 908779), Jul. 25, 1995.

Eckert, R.L. and E.A. Rorke, "Sequence of the Human Epidermal 58–kD (#5) Type II Keratin Reveals an Absence of 5' Upstream Sequence Conservation between Coexpressed Epidernal Keratins", *DNA*, 7: 337–345 (1988).

Eckert, R.L. and E.A. Rorke et al., (Direct Submission), GenBank Sequence Database (Accession M21389), National Center for Biotechnology Information, National Library of Medicine, Bethesda, Maryland, 20894, (GI 186697; GI 307082), Jan. 1993.

Lersch, R. et al., "Isolation, Sequence, and Expression of a Human Keratin K5 Gene: Transcriptional Regulation of Keratins and Insights into Pairwise Control", *Mol. Cell Biol.*, 9: 3685–3697 (1989).

Uttam, J. et al., "The genetic basis of epidermolysis bullosa simplex with mottled pigmentation", *Proc. Natl. Acad. Sci. USA*, 93: 9079–9084 (1996).

Bader, B.L., et al., "Amino acid sequence and gene organization of cytokeratin No. 19, an exceptional tail–less intermediate filament protein", *EMBO J.*, 5: 1865–1875 (1986).

Lussier, M. et al., "The mouse keratin 19–encoding gene: sequence, structure and chromosomal assignment", *Gene*, 95: 203–213 (1990).

Savtchenko, E.S. et al., "Embryonic Expression of the Human 40–kD Keratin: Evidence from a Processed Pseudogene Sequence", *Am. J. Hum. Genet.*, 43: 630–637 (1988).

Corden, L.D. and W.H.I. McLean, "Human keratin diseases: Hereditary fragility of specific epithelial tissues", *Exp. Dermatol.*, 5: 297–307 (1996).

Tomic–Canic, M. et al., "Novel Regulation of Keratin Gene Expression by Thyroid Hormone and Retinoid Receptors", *J. Biol. Chem.*, 271: 1416–1423 (1996).

Steinert, P.M. et al., "Self–assembly of Bovine Epidermal Keratin Filaments in Vitro", *J. Mol. Biol.*, 108–547–567 (1976).

*Primary Examiner*—Rebecca E. Prouty
*Assistant Examiner*—M. Monshipouri
(74) *Attorney, Agent, or Firm*—Incyte Genomics, Inc.; Lynn E. Murry; Colette Muenzen

(57) ABSTRACT

The invention provides human keratins (KERT) and polynucleotides which identify and encode KERT. The invention also provides expression vectors, host cells, antibodies, agonists, and antagonists. The invention also provides methods for diagnosing, treating or preventing disorders associated with expression of KERT.

5 Claims, 16 Drawing Sheets

```
                 9              18             27             36             45             54
5' CTT CTG CGT CCT GCT GAG CTC TGT TCT CTC CAG CAC CTC CCA ACC CAC TAG TGC 63             72             81             90             99            108
   CTG GTT CTC TTG CTC CAC CAG CAA GCC ACC ATG TCT CGC CAG TCA AGT GTG
                                                  M   S   R   Q   S   S   V 117            126            135            144            153            162
   TCC TTC CGG AGC GGG AGT CGT AGC TTC AGC ACC GCC TCT GCC ATC ACC CCG
    S   F   R   S   G   S   R   S   F   S   T   A   S   A   I   T   P 171            180            189            198            207            216
   TCT GTC TCC CGC ACC AGC TTC ACC TCC GTG TCC CGG TCC GGG GGT GGT GGT
    S   V   S   R   T   S   F   T   S   V   S   R   S   G   G   G   G 225            234            243            252            261            270
   GGT TTC GGC AGG GTC AGC CTT GCG GGT GCT TGT GGA GTG GGT GGT TAT GGC
    G   F   G   R   V   S   L   A   G   A   C   G   V   G   G   Y   G 279            288            297            306            315            324
   AGC CGG AGC CTC TAC AAC CTG GGG GGC TCC AAG AGG ATA TCC ATC AGC ACT AGT
    S   R   S   L   Y   N   L   G   G   S   K   R   I   S   I   S   T   S 333            342            351            360            369            378
   AGC CGG AGC TTC AGG AAC CGG TTT GGT GCT GGT GCT GGA GGC GGA GGC TAT GGC TTT
    S   R   S   F   R   N   R   F   G   A   G   A   G   G   G   G   Y   G   F
```

FIGURE 1A

```
      387       396       405       414       423       432
GGA GGT GGT GCC GGT AGT GGA TTT GGT TTC GGC GGT GGA GCT GGT GGT GGC TTT
 G   G   G   A   G   S   G   F   G   F   G   G   G   A   G   G   G   F 441       450       459       468       477       486
GGG CTC GGT GGC GGA GCT GGC TTT GGC GGA GGT GGC TTC GGT GGC CCT GGC TTT CCT
 G   L   G   G   G   A   G   F   G   G   G   G   F   G   G   P   G   F   P 495       504       513       522       531       540
GTC TGC CCT CCT GGA ATC CAA GAG GTC ACT AAC CAG AGT CTC CTG ACT
 V   C   P   P   G   I   Q   E   V   T   N   Q   S   L   L   T 549       558       567       576       585       594
CCC CTC AAC CTG CAA ATC GAC CCC AGC ATC CAG AGG GTG AGG ACC GAG GAG CGC
 P   L   N   L   Q   I   D   P   S   I   Q   R   V   R   T   E   E   R 603       612       621       630       639       648
GAG CAG ATC AAG ACC CTC AAC AAT AAG TTT GCC TCC TTC ATC GAC AAG GTG CGG
 E   Q   I   K   T   L   N   N   K   F   A   S   F   I   D   K   V   R 657       666       675       684       693       702
TTT CTG GAG CAG CAG AAC AAG AAG CTG GAG ACC AAG TGG ACG CTG CTG CAG GAG
 F   L   E   Q   Q   N   K   K   L   E   T   K   W   T   L   L   Q   E 711       720       729       738       747       756
CAG AAG TCG GCC AAG AGC CGC CTC CCA GAC ATC TTT GAG GCC CAG ATT GCT
 Q   K   S   A   K   S   R   L   P   D   I   F   E   A   Q   I   A
```

FIGURE 1B

```
      765              774              783              792              801              810
GGC CTT CGG GGT CAG CTT GAG GCA CTG CAG GTG GAT GGG GGC CGC CTG GAG GCG
 G   L   R   G   Q   L   E   A   L   Q   V   D   G   G   R   L   E   A 819              828              837              846              855              864
GAG CTG CGG AGC ATG CAG GAT GTG GAG GAC TTC AAG AAT AAG TAC GAA GAT
 E   L   R   S   M   Q   D   V   E   D   F   K   N   K   Y   E   D 873              882              891              900              909              918
GAA ATT AAC CAC CGC ACA GCT GCT GAG AAT GAG TTT GTG GTG CTG AAG AAG GAT
 E   I   N   H   R   T   A   A   E   N   E   F   V   V   L   K   K   D 927              936              945              954              963              972
GTG GAT GCT GCC TAC ATG AGC AAG GTG GAG CTG GAG GCC AAG GTG GAT GCC CTG
 V   D   A   A   Y   M   S   K   V   E   L   E   A   K   V   D   A   L 981              990              999             1008             1017             1026
AAT GAT GAG ATC AAC TTC CTC AGG ACC CTC AAT GAG ACG GAG TTG ACA GAG CTG
 N   D   E   I   N   F   L   R   T   L   N   E   T   E   L   T   E   L 1035             1044             1053             1062             1071             1080
CAG TCC CAG ATC TCC GAC ACA TCT GTG GTG CTG TCC ATG GAC AAC AGT CGC TCC
 Q   S   Q   I   S   D   T   S   V   V   L   S   M   D   N   S   R   S 1089             1098             1107             1116             1125             1134
CTG GAC CTG GAC GGC ATC ATC GCT GAG GTC AAG GCG CAG TAT GAG GAG ATG GCC
 L   D   L   D   G   I   I   A   E   V   K   A   Q   Y   E   E   M   A
```

FIGURE 1C

```
                         1143                  1152                  1161                  1170                  1179                  1188
AAA TGC AGC CGG GCT GAG GCT GAA GCC TGG TAC CAG ACC AAG TTT GAG ACC CTC
 K   C   S   R   A   E   A   E   A   W   Y   Q   T   K   F   E   T   L
                         1197                  1206                  1215                  1224                  1233                  1242
CAG GCC CAG GCT GGG AAG CAT GGG GAC GAC CTC CGG AAT ACC CGG AAT GAG ATT
 Q   A   Q   A   G   K   H   G   D   D   L   R   N   T   R   N   E   I
                         1251                  1260                  1269                  1278                  1287                  1296
TCA GAG ATG AAC CGG GCC ATC CAG AGG CTG CAG GCT GAG ATC GAC AAC ATC AAG
 S   E   M   N   R   A   I   Q   R   L   Q   A   E   I   D   N   I   K
                         1305                  1314                  1323                  1332                  1341                  1350
AAC CAG CGT GCC AAG TTG GAG GCC ATT GCC AAG CAG GAG GCT GAG GAG CGT GGG GAG
 N   Q   R   A   K   L   E   A   I   A   K   Q   E   A   E   E   R   G   E
                         1359                  1368                  1377                  1386                  1395                  1404
CTG GCG CTC AAG GAT GCT CGT GCC CGG CAG GAG CTG GAA GCC GCC CTG CAG
 L   A   L   K   D   A   R   A   R   Q   E   L   E   A   A   L   Q
                         1413                  1422                  1431                  1440                  1449                  1458
CGG GCC AAG CAG GAT ATG GCA CGG CAG CTG CGT GAG TAC CAG GAA CTC ATG AGC
 R   A   K   Q   D   M   A   R   Q   L   R   E   Y   Q   E   L   M   S
                         1467                  1476                  1485                  1494                  1503                  1512
GTG AAG CTG GCC CTG GAC ATC GAG ATC GCC ACC TAC CGC AAG CTG CTG GAG GGC
 V   K   L   A   L   D   I   E   I   A   T   Y   R   K   L   L   E   G
```

FIGURE 1D

```
            1521           1530           1539           1548           1557           1566
         GAG GAG AGC CGG TTG GCT GGA GAT GGA GTG GGA GCC GTG AAT ATC TCT GTG ATG
          E   E   S   R   L   A   G   D   G   V   G   A   V   N   I   S   V   M 1575           1584           1593           1602           1611           1620
         AAT TCC ACT GGT GGC AGT AGC AGT GGC GGT GGC ATT GGG CTG ACC CTC GGG GGA
          N   S   T   G   G   S   S   S   G   G   G   I   G   L   T   L   G   G 1629           1638           1647           1656           1665           1674
         ACC ATG GGC AGC AAT GCC CTG AGC TTC TCC AGC AGT GCG GGT CCT GGG CTC CTG
          T   M   G   S   N   A   L   S   F   S   S   S   A   G   P   G   L   L 1683           1692           1701           1710           1719           1728
         AAG GCT TAT TCC ATC CGG ACC GCA TCC GCC AGT CGC AGG AGT GCC CGC GAC TGA
          K   A   Y   S   I   R   T   A   S   A   S   R   R   S   A   R   D   *

1737           1746           1755           1764           1773           1782
         GCC GCC TCC CAC CAC TCC ACT CCT CCA GCC ACC CAC AAT CAC AAG AAG ATT 1791           1800           1809           1818           1827           1836
         CCC ACC CCT GCC TCC CAT GCC TGG TCC CAA GAC AGT GAG ACA GTC TGG AAA GTG 1845           1854           1863           1872
         ATG TCA GAA TAG CTT CCA ATA AAG CAC CTC ATT CTG AGC  3'
```

FIGURE 1E

```
                    11            20            29            38            47            56
5'CT GCC TGT ACC AGC CCA CCT CAG GTG CCT TCT CGC CGG CCT TCC TCA CCC ACC ATG
                                                                              M 65            74            83            92           101           110
TCT CGG CAG TCC TCC ATC ACC TTC CAG TCT GGC AGC CGC AGG TTC AGC ACC
 S   R   Q   S   S   I   T   F   Q   S   G   S   R   R   F   S   T 119           128           137           146           155           164
ACC TCG GCC ATC ACC CCG GCA GCT CCG GCC CGC TCC TTC AGC TCT GTC TCT GTG
 T   S   A   I   T   P   A   A   P   A   R   S   F   S   S   V   S   V 173           182           191           200           209           218
GCC CGC TCT GCA GCA GGG AGT GGG GGC CTG GGA AGG ATC AGC AGT GCT GGG GCC
 A   R   S   A   A   G   S   G   G   L   G   R   I   S   S   A   G   A 227           236           245           254           263           272
AGC TTT GGA AGC CGC AGC CTC TAC AAC CTG GGG GGT GCC AAG CGG GTC TCC CTC
 S   F   G   S   R   S   L   Y   N   L   G   G   A   K   R   V   S   L 281           290           299           308           317           326
AAT GGG TGT GGC AGC AGC TGC CGA AGT GGC TTT GGT GGC AGG GCC AGC AAC GGG
 N   G   C   G   S   S   C   R   S   G   F   G   G   R   A   S   N   G 335           344           353           362           371           380
TTT GGA GTC AAC AGT TTT GGA TAT GGA GGT GGA GTT GGA GGC TTC AGT
 F   G   V   N   S   F   G   Y   G   G   G   V   G   G   F   S
```

FIGURE 2A

```
      389        398        407        416    425        434
GGC CCC AGC TTC CCC GTG TGT CCT GGA GGC ATC CAA GAG GTC ACT GTC AAC
 G   P   S   F   P   V   C   P   G   G   I   Q   E   V   T   V   N 443        452        461    470        479        488
CAG AGT CTC CTG ACT CCT CTT CAC CTG CAA ATC GAC CCC ACC ATC CAG CGG GTG
 Q   S   L   L   T   P   L   H   L   Q   I   D   P   T   I   Q   R   V 497        506        515    524        533        542
CGG GCC GAG GAG CGC GAG CAG ATC AAG ACC CTC AAC AAT AAG TTC ACC TCC TTC
 R   A   E   E   R   E   Q   I   K   T   L   N   N   K   F   T   S   F 551        560        569    578        587        596
ATC GAC AAG GTG AGG TTC TTG GAG CAG CAG AAC AAG GTC CTG GAG ACC AAG TGG
 I   D   K   V   R   F   L   E   Q   Q   N   K   V   L   E   T   K   W 605        614        623    632        641        650
GCC CTC CTG CAG GAG CAG GGC TCC AGG ACT GTG AGG CAG AAC CTA GAG CCC CTC
 A   L   L   Q   E   Q   G   S   R   T   V   R   Q   N   L   E   P   L 659        668        677    686        695        704
TTT GAT TCC TAT ACC AGT GAG CTC CGA CGG CAG CTG GAA AGC ATC ACC ACC GAG
 F   D   S   Y   T   S   E   L   R   R   Q   L   E   S   I   T   T   E 713        722        731    740        749        758
AGG GGC AGG CTT GAA GCT GAA CTG AGG AAC ATG CAG GAT GTT GAA GAT TTC
 R   G   R   L   E   A   E   L   R   N   M   Q   D   V   E   D   F
```

FIGURE 2B

```
      767              776              785              794              803              812
AAA GTC AGG TAC GAA GAT GAA ATT AAC AAG CGC ACA GCT GCT GAG AAT GAA TTT
 K   V   R   Y   E   D   E   I   N   K   R   T   A   A   E   N   E   F 821              830              839              848              857              866
GTA GCC CTG AAA AAG GAC GTA GAT GCT GCC TAT ATG AAC AAG GTG GAG CTG GAA
 V   A   L   K   K   D   V   D   A   A   Y   M   N   K   V   E   L   E 875              884              893              902              911              920
GCC AAG GTC AAA TCT CTG CCT GAG GAG ATC AAC TTC ATC CAC TCA GTC TTT GAT
 A   K   V   K   S   L   P   E   E   I   N   F   I   H   S   V   F   D 929              938              947              956              965              974
GCA GAG CTG TCC CAG TTG CAG ACC CAG GTC GGT GAC ACA TCC GTG GTG CTG TCC
 A   E   L   S   Q   L   Q   T   Q   V   G   D   T   S   V   V   L   S 983              992             1001             1010             1019             1028
ATG GAC AAC AAC CGC AAC CTG GAC CTG GAT AGT ATC ATC GCC GAG GTC AAA GCA
 M   D   N   N   R   N   L   D   L   D   S   I   I   A   E   V   K   A 1037             1046             1055             1064             1073             1082
CAA TAC GAG GAC ATT GCC AAC CGC AGC CGG GCC GAG GCT GAG TCC TGG TAC CAG
 Q   Y   E   D   I   A   N   R   S   R   A   E   A   E   S   W   Y   Q 1091             1100             1109             1118             1127             1136
ACC AAG TAC GAG GAG CTG CAG GTC ACC GCA GGC AGA CAT GGG GAT GAC CTT CGA
 T   K   Y   E   E   L   Q   V   T   A   G   R   H   G   D   D   L   R
```

FIGURE 2C

```
       1145             1154             1163             1172             1181             1190
AAC ACC AAA CAA GAG ATC TCT GAA ATG AAC CGC ATG ATC CAG AGG CTG AGA GCT
 N   T   K   Q   E   I   S   E   M   N   R   M   I   Q   R   L   R   A 1199             1208             1217             1226             1235             1244
GAG ATT GAC AGC GTC AAG AAG CAG TGT TCC AGC TTG CAA ACG GCC ATT GCT GAT
 E   I   D   S   V   K   K   Q   C   S   S   L   Q   T   A   I   A   D 1253             1262             1271             1280             1289             1298
GCA GAG CAG CGG GGA GAA CTG GCT CTC AAG GAT GCA CGG GCC AAG CTG GTG GAC
 A   E   Q   R   G   E   L   A   L   K   D   A   R   A   K   L   V   D 1307             1316             1325             1334             1343             1352
CTT GAG GAG GCC CTG CAG AAG GCC CTG GAC ACG GCT CGG CTC CTG CGT GAG
 L   E   E   A   L   Q   K   A   L   D   T   A   R   L   L   R   E 1361             1370             1379             1388             1397             1406
TAC CAG GAG CTG ATG AAC ATC AAG CTG GCC CTG GAC GTG GAG ATC GCC ACC TAC
 Y   Q   E   L   M   N   I   K   L   A   L   D   V   E   I   A   T   Y 1415             1424             1433             1442             1451             1460
CGC AAG CTG CTG GAA GGC GAG GAG GAG TGC AGG TTG AGT GGA GAG GGA GTT TCT CCA
 R   K   L   L   E   G   E   E   E   C   R   L   S   G   E   G   V   S   P 1469             1478             1487             1496             1505             1514
GTT AAC ATT TCT GTC ACC TCT ACT CTT TCC AGT GGC TAT GGA CGC GGC AGC
 V   N   I   S   V   T   S   T   L   S   S   G   Y   G   R   G   S
```

FIGURE 2D

```
     1523           1532           1541      1550           1559           1568
AGC ATT GGA GGT GGA AAC CTG GGC CTC GGT GGG GGC AGC GGC TAC TCC TTC ACC
 S   I   G   G   G   N   L   G   L   G   G   G   S   G   Y   S   F   T 1577           1586           1595      1604           1613           1622
ACC AGT GGT GGG CAT AGC CTG GGT GCA GGC CTG GGA GGT TCT GGA TTC AGT GCC
 T   S   G   G   H   S   L   G   A   G   L   G   G   S   G   F   S   A 1631           1640           1649      1658           1667           1676
ACC AGC AAC CGG GGC TTA GGG GGC AGT GGT TCT AGC GTC AAG TTT GTC TCC ACC
 T   S   N   R   G   L   G   G   S   G   S   S   V   K   F   V   S   T 1685           1694           1703      1712           1721           1730
ACA TCC TCC AGC CAG AAG AGC TAC ACG CAC TAA GAG AGC CCC ATG GCT CCC TCT
 T   S   S   S   Q   K   S   Y   T   H   *

1739           1748           1757      1766           1775           1784
ACC CTG CCT TGA GGC CTG TTT GCA GTC ACA CCT GGA CAC CAG GGT CCT CCT CCT 1793           1802           1811      1820           1829           1838
TCC TCT CTC CTT GTA AGG TGC ACC TGT GCT GCT GGG AGC CTG GAG TAC TGG CTA 1847           1856           1865      1874           1883           1892
TAC CCA TTC CCA GGC CTA AGC CAG CCT CTC CCT GAC AGT GCC CAG ACT GCC
```

FIGURE 2E

```
              1901       1910       1919       1928       1937       1946
              AGC AGC ACC CGT CTG TTA CAC ATG TGA AAC CAA AGC CTG CTC TCT CCT AAG GCT 1955       1964       1973       1982       1991       2000
              CTC ATT CAG CCT ATC TTG CGA GGC CCG GGC AGC TGG AAA GTC CTC CTC CAG CTC 2009       2018       2027       2036       2045       2054
              CAC CTC CCT CCC TCC CTC CAG ATG CAG AGG CTG GGG AGT CTC TCA ATG CCA GGT 2063       2072       2081       2090       2099       2108
              TGT CAC CCA CCT GTC TCA TAG TGT TTA TAA GTG GCC TGC TGG GAG TGA GTG CTC 2117       2126       2135       2144       2153       2162
              CCT CTG TTC CCT CCC TGG AAT GTG TCT ATT AAA TGC ATG TGT CAC CTG AAA AAA

AAA AA 3'
```

FIGURE 2F

```
                                                        11          20          29          38          47          56
                                                 5'CG GTG CCA GGG AGT GGA GCA GAG CTC AGC CCC GTC CCA AAC ACA GAT GGG ACC ATG
                                                                                                                            M 65          74          83          92         101         110
   AAC TCC GGA CAC AGC TTC AGC CAG ACC CCC TCG GCC TCC TTC CAT GGC GCC GGA
     N   S   G   H   S   F   S   Q   T   P   S   A   S   F   H   G   A   G 119         128         137         146         155         164
   GGT GGC GGC CGG AGC CCC AGG AGC TTC CCC AGG GCT CCC ACC GTC CAT GGC GGT
     G   G   G   R   S   P   R   S   F   P   R   A   P   T   V   H   G   G 173         182         191         200         209         218
   GCG GGG GGA GCC CGC ATC TCC CTG TCC TTC ACC ACG CGG AGC TGC CCA CCC CCT
     A   G   G   A   R   I   S   L   S   F   T   T   R   S   C   P   P   P 227         236         245         254         263         272
   GGA GGG TCT TGG GGT TCT GGA AGA AGC AGC CCC CTA CTA GGC GGA AAT GGG AAG
     G   G   S   W   G   S   G   R   S   S   P   L   L   G   G   N   G   K 281         290         299         308         317         326
   GCC ACC ATG CAG AAT CTC AAC GAC CGC CTG GCC TCC TAC CTG GAG AAG GTT CGC
     A   T   M   Q   N   L   N   D   R   L   A   S   Y   L   E   K   V   R 335         344         353         362         371         380
  ʻGAG GAG GCC AAC ATG AAG CTG GAA AGC CGC ATC CTG AAA TGG CAC CAG
     E   E   A   N   M   K   L   E   S   R   I   L   K   W   H   Q
```

FIGURE 3A

```
    389       398       407       416       425       434
CAG AGA GAT CCT GGC AGT AAG AAA GAT TAT TCC CAG TAT GAG GAA AAC ATC ACA
 Q   R   D   P   G   S   K   K   D   Y   S   Q   Y   E   E   N   I   T 443       452       461       470       479       488
CAC CTG CAG GAG CAG CAG ATA GTG GAT GGT AAG ATG ACC AAT GCT CAG ATT CTT
 H   L   Q   E   Q   Q   I   V   D   G   K   M   T   N   A   Q   I   L 497       506       515       524       533       542
CTC ATT GAC AAT GCC AGG ATG GCA GTG GAT GAC TTC AAC CTC AAG TAT GAA AAT
 L   I   D   N   A   R   M   A   V   D   D   F   N   L   K   Y   E   N 551       560       569       578       587       596
GAA CAC TCC TTT AAG GAC TTG GAA ATT GAA GTC GAG GGC CTC CGA AGG ACC
 E   H   S   F   K   D   L   E   I   E   V   E   G   L   R   R   T 605       614       623       632       641       650
TTA GAC AAC CTG ACC ATT GTC ACA GAC CTA GAA CAG GAG CAG GAG GTG GAA GGA ATG
 L   D   N   L   T   I   V   T   D   L   E   Q   E   Q   E   V   E   G   M 659       668       677       686       695       704
AGG AAA GAG CTC ATT CTC ATG AAG AAG CAC CAT GAG CAG GAA ATG GAG AAG CAT
 R   K   E   L   I   L   M   K   K   H   H   E   Q   E   M   E   K   H 713       722       731       740       749       758
CAT GTG CCA AGT GAC TTC AAT GTC AAT GTG AAG GTG GAT ACA GGT CCC AGG GAA
 H   V   P   S   D   F   N   V   N   V   K   V   D   T   G   P   R   E
```

FIGURE 3B

```
GAT CTG ATT AAG GTC CTG GAG GAT ATG AGA CAA GAA TAT GAG CTT ATA ATA AAG
 D   L   I   K   V   L   E   D   M   R   Q   E   Y   E   L   I   I   K
767             776             785             794             803       812

AAG AAG CAT CGA GAC TTG GAC ACT TGG TAT AAA GAA CAG TCT GCA GCC ATG TCC
 K   K   H   R   D   L   D   T   W   Y   K   E   Q   S   A   A   M   S
821             830             839             848             857       866

CAG GAG GCA GCC AGT CCA GCC ACT GTG CAG AGC AGA CAA GGT GAC ATC CAC GAA
 Q   E   A   A   S   P   A   T   V   Q   S   R   Q   G   D   I   H   E
875             884             893             902             911       920

CTG AAG CGC ACA TTC CAG GCC CTG GAG ATT GAC CTG CAG ACA CAG TAC AGC ACG
 L   K   R   T   F   Q   A   L   E   I   D   L   Q   T   Q   Y   S   T
929             938             947             956             965       974

AAA TCT GCT TTG GAA AAC ATG TTA TCC GAG ACC CAG TCT CGG TAC TCC TGC AAG
 K   S   A   L   E   N   M   L   S   E   T   Q   S   R   Y   S   C   K
983             992             1001            1010            1019      1028

CTC CAG GAC ATG CAA GAG ATC ATC TCC CAC TAT GAG GAG GAA CTG ACG CAG CTA
 L   Q   D   M   Q   E   I   I   S   H   Y   E   E   E   L   T   Q   L
1037            1046            1055            1064            1073      1082

CGC CAT GAA CTG GAG CGG CAG AAC GAA TAC CAA GTG CTG CTG GGC ATC AAA
 R   H   E   L   E   R   Q   N   E   Y   Q   V   L   L   G   I   K
1091            1100            1109            1118            1127    1136
```

FIGURE 3C

```
      1145            1154            1163            1172            1181            1190
ACC CAC CTG GAG AAG GAA ATC ACC ACG TAC CGA CGG CTC CTG GAG GGA GAG AGT
 T   H   L   E   K   E   I   T   T   Y   R   R   L   L   E   G   E   S 1199            1208            1217            1226            1235            1244
GAA GGG ACA CGG GAA GAA TCA GAA TCG AAG ATG AGC AAA GTG TCT GCA ACT CCA AAG
 E   G   T   R   E   E   S   E   S   K   M   S   K   V   S   A   T   P   K 1253            1262            1271            1280            1289            1298
ATC AAG GCC ATA ACC CAG GAG ACC ATC AAC GGA AGA TTA GTT CTT TGT CAA GTG
 I   K   A   I   T   Q   E   T   I   N   G   R   L   V   L   C   Q   V 1307            1316            1325            1334            1343            1352
AAT GAA ATC CAA AAG CAC GCA TGA GAC CAA TGA AAG TTT CCG CCT GTT GTA AAA
 N   E   I   Q   K   H   A 1361            1370            1379            1388            1397            1406
TCT ATT TTC CCC CAA GGA AAG TCC TTG CAC AGA CAC CAG TGA GTG AGT TCT AAA 1415            1424            1433            1442            1451            1460
AGA TAC CCT TGG AAT TAT CAG ACT CAG AAA CTT TTA TTT TTT TCT GTA ACA 1469            1478            1487            1496            1505            1514
GTC TCA CCA GAC TTC TCA TAA TGC TCT TAA TAT ATT GCA CTT TTC TAA TCA AAG
```

FIGURE 3D

```
     1523      1532      1541      1550      1559      1568
TGC GAG TTT ATG AGG GTA AAG CTC TAC TTT CCT ACT GCA GCC TTC AGA TTC TCA 1577      1586      1595      1604      1613      1622
TCA TTT TGC ATC TAT TTT GTA GCC AAT AAA ACT CCG CAC TAG CAA AAA AAA AAA

HUMAN KERATINS

This application is a divisional application of U.S. application Ser. No. 09/067,351, filed Apr. 27, 1998, now U.S. Pat. No. 5,994,081 issued Nov. 30, 1999.

FIELD OF THE INVENTION

This invention relates to nucleic acid and amino acid sequences of human keratins and to the use of these sequences in the diagnosis, treatment, and prevention of epithelial, cell proliferative, developmental, and reproductive disorders.

BACKGROUND OF THE INVENTION

Keratins, members of the intermediate filament superfamily, are cytoskeletal proteins that assemble into approximately 10 nm diameter filaments that give structural support to epithelial cells. Intermediate filaments are so-named because their diameter is intermediate between those of microtubules and microfilaments. Keratins are abundant in soft epithelia such as skin and cornea, hard epithelia such as nails and hair, and in epithelia that line internal body cavities.

Keratins have a central α-helical rod region interrupted by short nonhelical linker segments. The rod region is bracketed, in most cases, by non-helical head and tail domains. The rod regions of two different keratin monomers associate to form a parallel coiled-coil heterodimer. A highly ordered assembly process leads from the heterodimers to the approximately 10 nm diameter intermediate filaments. (Lodish, H. et al. (1995) *Molecular Cell Biology*, Scientific American Books, New York, N.Y., pp. 1106–1116; and Fuchs, E. and Cleveland, D. W. (1998) Science 279:514–519.)

About thirty keratin genes have been identified, and these genes are differentially expressed in epithelial tissues at various stages of differentiation and development. (Fuchs, E. (1997) Mol. Biol. Cell 8:189–203.) Keratins are divided into Type I (acidic) and Type II (basic) families. In general keratins are expressed in pairs as the heterodimers form from one Type I keratin and one Type II keratin. Type II keratin 6 (K6) is a basic keratin which is coexpressed with Type I keratin 16 or Type I keratin 17. K6 is expressed in various normal tissues including filiform papillae of tongue, stratified epithelia lining the oral mucosa and esophagus, outer root sheath of hair follicles, and glandular epithelia. K6 expression, which appears to be associated with fast cell turnover rate, is induced in epidermis and other stratified epithelia that are undergoing hyperproliferation, for example wound healing, psoriasis, actinic keratosis, viral infections, and cancer. Multiple human isoforms of K6 have been identified. (Takahashi, K. et al. (1995) J. Biol. Chem. 270:18581–18592.)

Type II keratin 5 (K5) is coexpressed in stratified squamous epithelia with its assembly partner Type I keratin 14. (Eckert, R. L. and Rorke, E. A. (1988) DNA 7:337–345; and Lersch, R. et al. (1989) Mol. Cell Biol. 9:3685–3697.) Mutations in K5 cause the severe autosomal dominant skin blistering disorder epidermolysis bullosa simplex. (Uttam, J. et al. (1996) Proc. Natl. Acad. Sci. USA 93:9079–9084.)

Cytokeratin 19 (K19), the smallest known keratin, is a Type I keratin that differs from other keratins in that it lacks a carboxy-terminal nonhelical tail domain and does not have a designated partner keratin for filament formation. K19 is expressed in embryonic and adult simple epithelia and in stratified epithelia. (Bader, B. L. et al. (1986) EMBO J. 5:1865–1875; and Lussier, M. et al. (1990) Gene 95:203–213.) K19 may be expressed in the early human embryo. (Savtchenko, E. S. et al. (1988) Am. J. Hum. Genet. 43:630–637.)

Keratins are associated with many disease states. Mutations in keratin genes are responsible for skin diseases such as epidermolysis bullosa simplex, epidernolytic hyperkeratosis, ichthyosis bullosa of Siemens, epidermal nevi/epidermolytic hyperkeratosis type, and epidermolytic and nonepidermolytic palmoplantar keratoderma, some of which cause severe skin blistering. Keratin mutations are also responsible for pachyonychia congenita, a disease of the nails and hair, and for the hair disease monilethrix. Other disorders caused by keratin mutations include white sponge nevus, Meesmann's corneal dystrophy, chronic hepatitis/cryptogenic cirrhosis, and colorectal hyperplasia. (Fuchs and Cleveland, supra; Fuchs, supra; and Corden, L. E. and McLean, W. H. (1996) Exp. Dermatol. 5:297–307.)

Keratins are associated with cell proliferative disorders. As described above, K6 expression is induced in epidermis and other stratified epithelia that are undergoing hyperproliferation. Keratins may have roles in development and embryogenesis. K19, as well as keratins 8 and 18, may be expressed in the early human embryo. (Savtchenko, supra.) The expression of many keratin genes is controlled by retinoic acid, an important regulator of development and differentiation. (Tomic-Canic, M. et al. (1996) J. Biol. Chem. 271:1416–1423.)

The discovery of new human keratins and the polynucleotides encoding them satisfies a need in the art by providing new compositions which are useful in the diagnosis, treatment, and prevention of epithelial, cell proliferative, developmental, and reproductive disorders.

SUMMARY OF THE INVENTION

The invention features substantially purified polypeptides, human keratins, referred to collectively as "KERT" and individually as "KERT-1", "KERT-2", and "KERT-3". In one aspect, the invention provides a substantially purified polypeptide comprising an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention further provides a substantially purified variant having at least 90% amino acid identity to the amino acid sequences of SEQ ID NO:1, SEQ ID NO:2, or SEQ ID NO:3, or to a fragment of any of these sequences. The invention also provides an isolated and purified polynucleotide encoding the polypeptide comprising an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention also provides an isolated and purified polynucleotide comprising a polynucleotide sequence selected from the group consisting of SEQ ID NO:4, SEQ ID NO:5, SEQ ID NO:6, a fragment of SEQ ID NO:4, a fragment of SEQ ID NO:5, and a fragment of SEQ ID NO:6. The invention further provides an isolated and purified polynucleotide variant having at least 90% polynucleotide sequence identity to the polynucleotide sequence comprising a polynucleotide sequence selected from the group consisting of SEQ ID NO:4, SEQ ID NO:5, SEQ ID NO:6, a fragment of SEQ ID NO:4, a fragment of SEQ ID NO:5, and a fragment of SEQ ID NO:6, as well as an isolated and purified polynucleotide having a sequence which is complementary to the polynucleotide comprising a polynucleotide sequence selected from the group consisting of SEQ ID NO:4, SEQ ID NO:5, SEQ ID NO:6, a fragment of SEQ ID NO:4, a fragment of SEQ ID NO:5, and a fragment of SEQ ID NO:6.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:2, SEQ ID NO:3, a fragment of SEQ II) NO:1, a fragment of SEQ ID NO:2, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3, as well as a purified agonist and a purified antagonist to the polypeptide.

The invention also provides a method for treating or preventing an epithelial disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention also provides a method for treating or preventing a cell proliferative disorder, the method comprising administering to a subject in need of such treatment an effective amount of an antagonist of the polypeptide having an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention also provides a method for treating or preventing a developmental disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention also provides a method for treating or preventing a reproductive disorder, the method comprising administering to a subject in need of such treatment an effective amount of an antagonist of the polypeptide having an amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3.

The invention also provides a method for detecting a polynucleotide encoding the polypeptide comprising the amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, SEQ ID NO:3, a fragment of SEQ ID NO:1, a fragment of SEQ ID NO:2, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:4) of KERT-1. The alignment was produced using MACDNASIS PRO software (Hitachi Software Engineering, South San Francisco, Calif.).

FIGS. 2A, 2B, 2C, 2D, 2E, and 2F show the amino acid sequence (SEQ ID NO:2) and nucleic acid sequence (SEQ ID NO:5) of KERT-2.

FIGS. 3A, 3B, 3C, 3D, and 3E show the amino acid sequence (SEQ ID NO:3) and nucleic acid sequence (SEQ ID NO:6) of KERT-3.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"KERT," as used herein, refers to the amino acid sequences of substantially purified KERT obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to KERT, increases or prolongs the duration of the effect of KERT. Agonists may include proteins, nucleic acids, carbohydrates, or any other molecules which bind to and modulate the effect of KERT.

An "allelic variant", as this term is used herein, is an alternative form of the gene encoding KERT. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding KERT, as described herein, include those sequences with deletions, insertions, or substitutions of different nucleotides, resulting in a polynucleotide the same as KERT or a polypeptide with at least one functional characteristic of KERT. Included within this definition are polymorphisms which may or may not be readily detectable using a particular oligonucleotide probe of the polynucleotide encoding KERT, and improper or unexpected hybridization to allelic variants, with a locus other than the normal chromosomal locus for the polynucleotide sequence encoding KERT. The encoded protein may also be "altered" and may contain deletions, insertions, or substitutions of amino acid residues which produce a silent change and result in a functionally equivalent KERT. Deliberate amino acid substitutions may be made on the basis of similarity in polarity, charge, solubility, hydrophobicity, hydrophilicity, and/or the amphipathic nature of the residues, as long as the biological or immunological activity of KERT is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence", as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of KERT which are preferably about 5 to about 15 amino acids in length, most preferably 14 amino acids, and which retain some biological activity or immunological activity of KERT. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification", as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp. 1–5.)

The term "antagonist", as it is used herein, refers to a molecule which, when bound to KERT, decreases the amount or the duration of the effect of the biological or immunological activity of KERT. Antagonists may include proteins, nucleic acids, carbohydrates, antibodies, or any other molecules which decrease the effect of KERT.

As used herein, the term "antibody" refers to intact molecules as well as to fragments thereof, such as Fab, F(ab')$_2$, and Fv fragments, which are capable of binding the epitopic determinant. Antibodies that bind KERT polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense", as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active" refers to a protein having structural, regulatory, or biochemical functions of a naturally occurring molecule. Likewise, "immunologically active" refers to the capability of the natural, recombinant, or synthetic KERT, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence", as these terms are used herein, refer broadly to any composition containing the given polynucleotide or amino acid sequence. The composition may comprise a dry formulation, an aqueous solution, or a sterile composition. Compositions comprising polynucleotide sequences encoding KERT or fragments of KERT may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence", as used herein, refers to a nucleic acid sequence which has been resequenced to resolve uncalled bases, extended using XL-PCR kit (PE Biosystems, Foster City, Calif.) in the 5' and/or the 3' direction, and resequenced, or which has been assembled from the overlapping sequences of more than one Incyte Clone using a computer program for fragment assembly, such as the GEL-VIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding KERT by northern analysis, is indicative of the presence of nucleic acids encoding KERT in a sample and thereby correlates with expression of the transcript from the polynucleotide encoding KERT.

A "deletion", as the term is used herein, refers to a change in the amino acid or nucleotide sequence that results in the absence of one or more amino acid residues or nucleotides.

The term "derivative", as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity", as used herein, refers to a degree of complementarity. There may be partial similarity or complete similarity. The word "identity" may substitute for the word "similarity". A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison, Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nature Genet. 15:345–355.)

The term "humanized antibody", as used herein, refers to antibody molecules in which the amino acid sequence in the non-antigen binding regions has been altered so that the antibody more closely resembles a human antibody, and still retains its original binding ability.

"Hybridization", as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition", as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray", as used herein, refers to an arrangement of distinct polynucleotides arrayed on a substrate, e.g., paper, nylon or any other type of membrane, filter, chip, glass slide, or any other suitable solid support.

The terms "element" or "array element", as used herein, in a microarray context, refer to hybridizable polynucleotides arranged on the surface of a substrate.

The term "modulate", as it appears herein, refers to a change in the activity of KERT. For example, modulation may cause an increase or a decrease in protein activity, binding characteristics, or any other biological, functional, or immunological properties of KERT.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked", as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide", as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer", "primer", "oligomer", and "probe", as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.) The term "sample", as used herein, is used in its broadest sense. A biological sample suspected of containing nucleic acids encoding KERT, or fragments thereof, or KERT itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A", the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified", as used herein, refers to nucleic acid or amino acid sequences that are removed from their natural environment and are isolated or separated, and are at least about 60% free, preferably about 75% free, and most preferably about 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of KERT, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The Invention

The invention is based on the discovery of new human keratins (KERT), the polynucleotides encoding KERT, and the use of these compositions for the diagnosis, treatment, or prevention of epithelial disorders, cell proliferative disorders, developmental disorders, and reproductive disorders.

Nucleic acids encoding the KERT-1 of the present invention were first identified in Incyte Clone 1467090 from a pancreatic tumor tissue cDNA library (PANCTUT02) using a computer search for amino acid sequence alignments. A consensus sequence, SEQ ID NO:4, was derived from the following overlapping and/or extended nucleic acid sequences: Incyte Clones 1467090 (PANCTUT02), 3564721 (SKINNOT05), 550748 and 551305 (BEPINOT01), 1211624 (BRSTNOT02), 1432368 and 1434337 (BEPINON01), and 1315079 (BLADTUT02).

In one embodiment, the invention encompasses a polypeptide comprising the amino acid sequence of SEQ ID NO:1. KERT-1 is 546 amino acids in length. PFAM analysis shows that KERT-1 resembles intermediate filament proteins in the region from residues E167 through R479. KERT-1 has a potential intermediate filaments signature at I466ATYRKLLE; four potential N-glycosylation sites at residues N146, N306, N489, and N494; one potential cAMP- and cGMP-dependent protein kinase phosphorylation site at S75; nine potential casein kinase II phosphorylation sites at residues S181, S245, T265, S284, T304, S352, T362, T381, and S543; ten potential protein kinase C phosphorylation sites at residues S8, S71, S82, S208, S211, S457, T468, S533, S540, and S543; and two potential tyrosine kinase phosphorylation sites at residues Y282 and Y360. KERT-1 has chemical and structural homology with a human keratin type II (#5) protein (GI 307082). Specifically, KERT-1 shares 77% sequence identity with human keratin type II (#5) protein. A fragment of SEQ ID NO:4 from about nucleotide 805 to about nucleotide 834 is useful, for example, as a hybridization probe. Northern analysis shows the expression of this sequence in various libraries, at least 66% of which are immortalized or cancerous, at least 20% of which involve immune response, and at least 17% of which involve fetal or proliferating cells. Of particular note is the expression of KERT-1 in libraries derived from male reproductive, female reproductive, cardiovascular, gastrointestinal, dermatologic, and developmental tissues.

Nucleic acids encoding the KERT-2 of the present invention were first identified in Incyte Clone 2029060 from an epidermal breast keratinocytes (NHEK) cDNA library (KERANOT02) using a computer search for amino acid sequence alignments. A consensus sequence, SEQ ID NO:5, was derived from the following overlapping and/or extended nucleic acid sequences: Incyte Clones 2029060, 822239 and 818789 (KERANOT02), and shotgun sequences SAEB00569, SAEB02278, and SAEB02270.

In one embodiment, the invention encompasses a polypeptide comprising the amino acid sequence of SEQ ID NO:2. KERT-2 is 551 amino acids in length. PFAM analysis shows that KERT-2 resembles intermediate filament proteins in the region from residue E148 to R461. KERT-2 has a potential intermediate filaments signature at I448ATYRKLLE; three potential N-glycosylation sites at residues N127, N332, and N471; one potential cAMP- and cGMP-dependent protein kinase phosphorylation site at residue S72; seven potential casein kinase II phosphorylation sites at residues S162, T247, S276, S286, S334, T344, and T363; ten potential protein kinase C phosphorylation sites at residues S13, S79, T191, T216, S383, T427, T450, S525, S535, and S545; and two potential tyrosine kinase phosphorylation sites at residues Y264 and Y342. KERT-2 has chemical and structural homology with a human type keratin 6 protein (GI 908779). Specifically, KERT-2 shares 70% sequence identity with human type II keratin 6 protein. A fragment of SEQ ID NO:5 from about nucleotide 57 to about nucleotide 83 is useful, for example, as a hybridization probe. Northern analysis shows the expression of this sequence in various libraries, at least 33% of which are immortalized or cancerous, at least 17% of which involve immune response, and at least 50% of which involved fetal or proliferating cells. Of particular note is the expression of KERT-2 in libraries derived from dermatologic, cardiovascular, developmental, gastrointestinal, and male reproductive tissues.

Nucleic acids encoding the KERT-3 of the present invention were first identified in Incyte Clone 2124178 from a diseased breast tissue cDNA library (BRSTNOT07) using a computer search for amino acid sequence alignments. A consensus sequence, SEQ ID NO:6, was derived from the following overlapping and/or extended nucleic acid sequences: Incyte Clones 2124178 (BRSTNOT07), 2631369 (COLNTUT15), 1901262 (BLADTUT06), 1950519 (PITUNOT01), 2373591 (ISLTNOT01), 642395 (BRSTNOT03), and 3092785 (BRSTNOT19).

In one embodiment, the invention encompasses a polypeptide comprising the amino acid sequence of SEQ ID NO:3. KERT-3 is 422 amino acids in length. PFAM analysis shows that KERT-3 resembles intermediate filament proteins in the region from residue N71 to residue G381. KERT-3 has a potential intermediate filaments signature at I368TTYRRLLE; two potential N-glycosylation sites at residues N125 and N184; eight potential casein kinase II phosphorylation sites at residues S85, S1 15, S120, T190, S309, S334, T362, and T382; nine potential protein kinase C phosphorylation sites at residues T48, S61, S115,S166, S306,S323, T370, S389, and T395; and one potential tyrosine kinase phosphorylation site at residue Y263. KERT-3 has chemical and structural homology with bovine cytokeratin 19 (GI 1197196). Specifically, KERT-3 shares about 42% sequence identity with bovine cytokeratin 19. A fragment of SEQ ID NO:6 from about nucleotide 57 to about nucleotide 86 is useful, for example, as a hybridization probe. Northern analysis shows the expression of this sequence in various libraries, at least 64% of which are immortalized or cancerous, at least 21% of which involve immune response, and at least 14% of which involve fetal or proliferating cells. Of particular note is the expression of KERT-3 in libraries derived from male reproductive, female reproductive, gastrointestinal, and developmental tissues.

The invention also encompasses KERT variants. A preferred KERT variant is one which has at least about 80%, more preferably at least about 90%, and most preferably at least about 95% amino acid sequence identity to the KERT amino acid sequence, and which contains at least one functional or structural characteristic of KERT.

The invention also encompasses polynucleotides which encode KERT. In a particular embodiment, the invention encompasses a polynucleotide sequence comprising the sequence of SEQ ID NO:4, as shown in FIGS. 1A, 1B, 1C, 1D, and 1E, which encodes a KERT. In a further embodiment, the invention encompasses the polynucleotide sequence comprising the sequence of SEQ ID NO:5, as shown in FIGS. 2A, 2B, 2C, 2D, 2E, and 2F, which encodes a KERT. In a further embodiment, the invention encompasses the polynucleotide sequence comprising the sequence of SEQ ID NO:6, a shown in FIGS. 3A, 3B, 3C, 3D, and 3E, which encodes a KERT.

The invention also encompasses a variant of a polynucleotide sequence encoding KERT. In particular, such a variant polynucleotide sequence will have at least about 80%, more preferably at least about 90%, and most preferably at least about 95% polynucleotide sequence identity to the polynucleotide sequence encoding KERT. A particular aspect of the invention encompasses a variant of SEQ ID NO:4 which has at least about 80%, more preferably at least about 90%, and most preferably at least about 95% polynucleotide sequence identity to SEQ ID NO:4. The invention further encompasses a polynucleotide variant of SEQ ID NO:5 having at least about 80%, more preferably at least about 90%, and most preferably at least about 95% polynucleotide sequence identity to SEQ ID NO:5. The invention further encompasses a polynucleotide variant of SEQ ID NO:6 having at least about 80%, more preferably at least about 90%, and most preferably at least about 95% polynucleotide sequence identity to SEQ ID NO:6. Any one of the polynucleotide variants described above can encode an amino acid sequence which contains at least one functional or structural characteristic of KERT.

It will be appreciated by those skilled in the art that as a result of the degeneracy of the genetic code, a multitude of polynucleotide sequences encoding KERT, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring KERT, and all such variations are to be considered as being specifically disclosed.

Although nucleotide sequences which encode KERT and its variants are preferably capable of hybridizing to the nucleotide sequence of the naturally occurring KERT under appropriately selected conditions of stringency, it may be advantageous to produce nucleotide sequences encoding KERT or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding KERT and its derivatives without altering the encoded amino acid sequences include the production of RNA transcripts having more desirable properties, such as a greater half-life, than transcripts produced from the naturally occurring sequence.

The invention also encompasses production of DNA sequences which encode KERT and KERT derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding KERT or any fragment thereof.

Also encompassed by the invention are polynucleotide sequences that are capable of hybridizing to the claimed polynucleotide sequences, and, in particular, to those shown in SEQ ID NO:4, SEQ ID NO:5, SEQ ID NO:6, a fragment of SEQ ID NO:4, a fragment of SEQ ID NO:5, or a fragment of SEQ ID NO:6 under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE enzyme, Taq polymerase, and thermostable T7 DNA polymerase (Amersham Pharmacia Biotech, Piscataway N.J.), or combinations of polymerases and proofreading exonucleases such as those found in the ELONGASE Amplification System (Life Technologies, Gaithersburg, Md.). Preferably, the process is automated with machines such as the MICROLAB 2200 (Hamilton, Reno, Nev.), DNA ENGINE thermal cycler (PTC200; MJ Research, Watertown, Mass.) and the ABI CATALYST and PRISM 373 and 377 DNA sequencing systems (PE Biosystems).

The nucleic acid sequences encoding KERT may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto, Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, PE Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode KERT may be cloned in recombinant DNA molecules that direct expression of KERT, or fragments or functional equivalents thereof, in appropriate host cells. Due to the inherent degeneracy of the genetic code, other DNA sequences which encode substantially the same or a functionally equivalent amino acid sequence may be produced and used to express KERT.

The nucleotide sequences of the present invention can be engineered using methods generally known in the art in order to alter KERT-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding KERT may be synthesized, in whole or in part, using chemical methods well known in the art. (See, e.g., Caruthers, M. H. et al. (1980) Nucleic Acids Symp. Ser. (7) 215–223, and Horn, T. et al. (1980) Nucleic Acids Symp. Ser. (7) 225–232.) Alternatively, KERT itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide synthesizer (PE Biosystems). Additionally, the amino acid sequence of KERT, or any part thereof, may be altered during direct synthesis and/or combined with sequences from other proteins, or any part thereof, to produce a variant polypeptide.

The peptide may be substantially purified by preparative high performance liquid chromatography. (See, E.g., Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties,* WH Freeman and Co., New York, N.Y.)

In order to express a biologically active KERT, the nucleotide sequences encoding KERT or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding KERT. Such elements may vary in their strength and specificity. Specific initiation signals may also be used to achieve more efficient translation of sequences encoding KERT. Such signals include the ATG initiation codon and adjacent sequences, e.g. the Kozak sequence. In cases where sequences encoding KERT and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding KERT and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding KERT. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding KERT. For example, routine cloning, subcloning, and propagation of polynucleotide sequences encoding KERT can be achieved using a multifunctional *E. coli* vector such as BLUESCRIPT phagemid (Stratagene, La Jolla, Calif.) or pSPORT 1 plasmid (Life Technologies). Ligation of sequences encoding KERT into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of KERT are needed, e.g. for the production of antibodies, vectors which direct high level expression of KERT may be used. For example, vectors containing the strong, inducible T5 or T7 bacteriophage promoter may be used.

Yeast expression systems may be used for production of KERT. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of KERT. Transcription of sequences encoding KERT may be driven viral promoters, e.g., the 35S and 19S promoters of CAMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding KERT may be ligated into an adenovirus transcription/translation complex consisting of the late promoter and tripartite leader sequence. Insertion in a non-essential E1 or E3 region of the viral genome may be used to obtain infective virus which expresses KERT in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of KERT in cell lines is preferred. For example, sequences encoding KERT can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding KERT is inserted within a marker gene sequence, transformed cells containing sequences encoding KERT can be identified by the absence of marker gene function. Alternatively, a marker gene can be placed in tandem with a sequence encoding KERT under the control of a single promoter. Expression of the marker gene in response to induction or selection usually indicates expression of the tandem gene as well.

In general, host cells that contain the nucleic acid sequence encoding KERT and that express KERT may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of KERT using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on KERT is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding KERT include oligolabeling, nick translation, end-labeling, or PCR amplification using a labeled nucleotide. Alternatively, the sequences encoding KERT, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech and Promega (Madison, Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding KERT may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode KERT may be designed to contain signal sequences which direct secretion of KERT through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Manassas, Md.) and may be chosen to ensure the correct modification and processing of the foreign protein.

In another embodiment of the invention, natural, modified, or recombinant nucleic acid sequences encoding KERT may be ligated to a heterologous sequence resulting in translation of a fusion protein in any of the aforementioned host systems. For example, a chimeric KERT protein containing a heterologous moiety that can be recognized by a commercially available antibody may facilitate the screening of peptide libraries for inhibitors of KERT activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin. GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin enable immunoaffinity purification of fusion proteins using commercially available monoclonal and polyclonal antibodies that specifically recognize these epitope tags. A fusion protein may also be engineered to contain a proteolytic cleavage site located between the KERT encoding sequence and the heterologous protein sequence, so that KERT may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled KERT may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of KERT may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431A Peptide synthesizer (PE Biosystems). Various fragments of KERT may be synthesized separately and then combined to produce the full length molecule.

Therapeutics

Chemical and structural similarity exists between KERT-1 and keratin type II (#5) from human (GI 307082). In addition, KERT-1 is expressed in cancerous, fetal or proliferating, reproductive, dermatologic, and developmental tissues. Therefore, KERT-1 appears to play a role in epithelial, cell proliferative, developmental, and reproductive disorders.

Chemical and structural similarity exists between KERT-2 and type II keratin 6 protein from human (GI 908779). In addition, KERT-2 is expressed in cancerous, fetal or proliferating, dermatologic, developmental, and reproductive tissues. Therefore, KERT-2 appears to play a role in epithelial, cell proliferative, developmental, and reproductive disorders.

Chemical and structural similarity exists between KERT-3 and cytokeratin 19 from bovine (GI 1197196). In addition, KERT-3 is expressed in cancerous, fetal or proliferating, reproductive, and developmental tissues. Therefore, KERT-3 appears to play a role in epithelial, cell proliferative, developmental, and reproductive disorders.

Therefore, in one embodiment, KERT or a fragment or derivative thereof may be administered to a subject to treat or prevent an epithelial disorder. Such epithelial disorders can include, but are not limited to, dyshidrotic eczema, allergic contact dermatitis, keratosis pilaris, melasma, vitiligo, actinic keratosis, basal cell carcinoma, squamous cell carcinoma, seborrheic keratosis, folliculitis, herpes simplex, herpes zoster, varicella, candidiasis, dermatophytosis, scabies, insect bites, cherry angioma, keloid, dermatofibroma, acrochordons, urticaria, transient acantholytic dermatosis, xerosis, eczema, atopic dermatitis, contact dermatitis, hand eczema, nummular eczema, lichen simplex chronicus, asteatotic eczema, stasis dermatitis and stasis ulceration, seborrheic dermatitis, psoriasis, lichen planus, pityriasis rosea, impetigo, ecthyma, dermatophytosis, tinea versicolor, warts, acne vulgaris, acne rosacea, pemphigus vulgaris, pemphigus foliaceus, paraneoplastic pemphigus, bullous pemphigoid, herpes gestationis, dermatitis herpetiformis, linear IgA disease, epidermolysis bullosa acquisita, dermatomyositis, lupus erythematosus, scleroderma and morphea, erythroderma, alopecia, figurate skin lesions, telangiectasias, hypopigmentation, hyperpigmentation, vesicles/bullae, exanthems, cutaneous drug reactions, papulonodular skin lesions, photosensitivity diseases, epidermolysis bullosa simplex, epidermolytic hyperkeratosis, epidermolytic and nonepidermolytic palmoplantar keratoderma, ichthyosis bullosa of Siemens, ichthyosis exfoliativa, keratosis palmaris et plantaris, keratosis palmoplantaris, palmoplantar keratoderma, keratosis punctata, Meesmann's corneal dystrophy, pachyonychia congenita, white sponge nevus, steatocystoma multiplex, epidermal nevilepidermolytic hyperkeratosis type, monilethrix, chronic hepatitis/cryptogenic cirrhosis, and colorectal hyperplasia.

In another embodiment, a vector capable of expressing KERT or a fragment or derivative thereof may be administered to a subject to treat or prevent an epithelial disorder including, but not limited to, those described above.

In a further embodiment, a pharmaceutical composition comprising a substantially purified KERT in conjunction with a suitable pharmaceutical carrier may be administered to a subject to treat or prevent an epithelial disorder including, but not limited to, those provided above.

In still another embodiment, an agonist which modulates the activity of KERT may be administered to a subject to treat or prevent an epithelial disorder including, but not limited to, those listed above.

In a further embodiment, an antagonist of KERT may be administered to a subject to treat or prevent a cell proliferative disorder. Such a cell proliferative disorder may include, but is not limited to, actinic keratosis, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds KERT may be used directly as an antagonist or indirectly as a targeting or delivery mechanism for bringing a pharmaceutical agent to cells or tissue which express KERT.

In an additional embodiment, a vector expressing the complement of the polynucleotide encoding KERT may be administered to a subject to treat or prevent a cell proliferative disorder including, but not limited to, those described above.

Therefore, in one embodiment, KERT or a fragment or derivative thereof may be administered to a subject to treat or prevent a developmental disorder. Such developmental disorders can include, but are not limited to, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss.

In another embodiment, a vector capable of expressing KERT or a fragment or derivative thereof may be administered to a subject to treat or prevent a developmental disorder including, but not limited to, those described above.

In a further embodiment, a pharmaceutical composition comprising a substantially purified KERT in conjunction with a suitable pharmaceutical carrier may be administered to a subject to treat or prevent a developmental disorder including, but not limited to, those provided above.

In still another embodiment, an agonist which modulates the activity of KERT may be administered to a subject to treat or prevent a developmental disorder including, but not limited to, those listed above.

In a further embodiment, an antagonist of KERT may be administered to a subject to treat or prevent a reproductive disorder. Such a reproductive disorder may include, but is not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. In one aspect, an antibody which specifically binds KERT may be used directly as an antagonist or indirectly as a targeting or delivery mechanism for bringing a pharmaceutical agent to cells or tissue which express KERT.

In an additional embodiment, a vector expressing the complement of the polynucleotide encoding KERT may be administered to a subject to treat or prevent a reproductive disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of KERT may be produced using methods which are generally known in the art. In particular, purified KERT may be used to produce antibodies or to screen libraries of pharmaceutical agents to identify those which specifically bind KERT. Antibodies to KERT may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with KERT or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to KERT have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of KERT amino acids may be fused with those of another protein, such as KLH, and antibodies to the chimeric molecule may be produced.

Monoclonal antibodies to KERT may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R.J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce KERT-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for KERT may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between KERT and its specific antibody. A two-site, monoclonal-based immunoassay utilizing monoclonal antibodies reactive to two non-interfering KERT epitopes is preferred, but a competitive binding assay may also be employed. (Maddox, supra.)

In another embodiment of the invention, the polynucleotides encoding KERT, or any fragment or complement thereof, may be used for therapeutic purposes. In one aspect, the complement of the polynucleotide encoding KERT may be used in situations in which it would be desirable to block the transcription of the mRNA. In particular, cells may be transformed with sequences complementary to polynucleotides encoding KERT. Thus, complementary molecules or fragments may be used to modulate KERT activity, or to achieve regulation of gene function. Such technology is now well known in the art, and sense or antisense oligonucleotides or larger fragments can be designed from various locations along the coding or control regions of sequences encoding KERT.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding KERT. (See, e.g., Sambrook, supra; and Ausubel, supra.)

Genes encoding KERT can be turned off by transforming a cell or tissue with expression vectors which express high levels of a polynucleotide, or fragment thereof, encoding KERT. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding KERT. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) In: Huber, B. E. And B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding KERT.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding KERT. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of KERT, antibodies to KERT, and mimetics, agonists, antagonists, or inhibitors of KERT. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of KERT, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example KERT or fragments thereof, antibodies of KERT, and agonists, antagonists or inhibitors of KERT, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind KERT may be used for the diagnosis of disorders characterized by expression of KERT or in assays to monitor patients being treated with KERT or agonists, antagonists, or inhibitors of KERT. Antibodies useful for diagnostic purposes may be prepared in the same manner as described above for therapeutics. Diagnostic assays for KERT include methods which utilize the antibody and a label to detect KERT in human body fluids or in extracts of cells or tissues. The antibodies may be used with or without modification and may be labeled by covalent or non-covalent attachment of a reporter molecule. A wide variety of reporter molecules, several of which are described above, are known in the art and may be used.

A variety of protocols for measuring KERT, including ELISAs, RIAs, and FACS, are known in the art and provide a basis for diagnosing altered or abnormal levels of KERT expression. Normal or standard values for KERT expression are established by combining body fluids or cell extracts taken from normal mammalian subjects, preferably human, with antibody to KERT under conditions suitable for complex formation. The amount of standard complex formation may be quantitated by various methods, preferably by photometric means. Quantities of KERT expressed in subject, control, and disease samples from biopsied tissues are compared with the standard values. Deviation between standard and subject values establishes the parameters for diagnosing disease.

In another embodiment of the invention, the polynucleotides encoding KERT may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of KERT may be correlated with disease. The diagnostic assay may be used to determine absence, presence, and excess expression of KERT, and to monitor regulation of KERT levels during therapeutic intervention.

In one aspect, hybridization with PCR probes which are capable of detecting polynucleotide sequences, including genomic sequences, encoding KERT or closely related molecules may be used to identify nucleic acid sequences which encode KERT. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding KERT, allelic variants, or related sequences.

Probes may also be used for the detection of related sequences, and should preferably have at least 50% sequence identity to any of the KERT encoding sequences. The hybridization probes of the subject invention may be DNA or RNA and may be derived from the sequence of SEQ ID NO:4, SEQ ID NO:5, or SEQ ID NO:6 or from genomic sequences including promoters, enhancers, and introns of the KERT gene.

Means for producing specific hybridization probes for DNAs encoding KERT include the cloning of polynucleotide sequences encoding KERT or KERT derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidintbiotin coupling systems, and the like.

Polynucleotide sequences encoding KERT may be used for the diagnosis of a disorder associated with expression of KERT. Examples of such a disorder include, but are not limited to, epithelial disorders such as dyshidrotic eczema, allergic contact dermatitis, keratosis pilaris, melasma, vitiligo, actinic keratosis, basal cell carcinoma, squamous cell carcinoma, seborrheic keratosis, folliculitis, herpes simplex, herpes zoster, varicella, candidiasis, dermatophytosis, scabies, insect bites, cherry angioma, keloid, dermatofibroma, acrochordons, urticaria, transient acantholytic dermatosis, xerosis, eczema, atopic dermatitis, contact dermatitis, hand eczema, nummular eczema, lichen simplex chronicus, asteatotic eczema, stasis dermatitis and stasis ulceration, seborrheic dermatitis, psoriasis, lichen planus, pityriasis rosea, impetigo, ecthyma, dermatophytosis, tinea versicolor, warts, acne vulgaris, acne rosacea, pemphigus vulgaris, pemphigus foliaceus, paraneoplastic pemphigus, bullous pemphigoid, herpes gestationis, dermatitis herpetiformis, linear IgA disease, epidermolysis bullosa acquisita, dermatomyositis, lupus erythematosus, scleroderma and morphea, erythroderma, alopecia, figurate skin lesions, telangiectasias, hypopigmentation, hyperpigmentation, vesicles/bullae, exanthems, cutaneous drug reactions, papulonodular skin lesions, photosensitivity diseases, epidermolysis bullosa simplex, epidermolytic hyperkeratosis, epidermolytic and nonepidermolytic palmoplantar keratoderma, ichthyosis bullosa of Siemens, ichthyosis exfoliativa, keratosis palmaris et plantaris, keratosis palmoplantaris, palmoplantar keratoderma, keratosis punctata, Meesmann's corneal dystrophy, pachyonychia congenita, white sponge nevus, steatocystoma multiplex, epidermal nevi/epidermolytic hyperkeratosis type, monilethrix, chronic hepatitis/cryptogenic cirrhosis, and colorectal hyperplasia; cell proliferative disorders such as actinic keratosis, arteriosclerosis, atherosclerosis, bursitis, cirrhosis, hepatitis, mixed connective tissue disease, myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss; and reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. The polynucleotide sequences encoding KERT may be used in Southern or Northern analysis, dot blot, or other membrane-based technologies; in PCR technologies; in dipstick, pin, and ELISA-like assays; and in microarrays utilizing fluids or tissues from patients to detect altered KERT expression. Such qualitative or quantitative methods are well known in the art.

In a particular aspect, the nucleotide sequences encoding KERT may be useful in assays that detect the presence of associated disorders, particularly those mentioned above. The nucleotide sequences encoding KERT may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding KERT in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of KERT, a normal or standard profile for expression is established. This may be accomplished by combining body fluids or cell extracts taken from normal subjects, either animal or human, with a sequence, or a fragment thereof, encoding KERT, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding KERT may involve the use of PCR. These oligomers may be chemically synthesized, generated enzymatically, or produced in vitro. Oligomers will preferably contain a fragment of a polynucleotide encoding KERT, or a fragment of a polynucleotide complementary to the polynucleotide encoding KERT, and will be employed under optimized conditions for identification of a specific gene or condition. Oligomers may also be employed under less stringent conditions for detection or quantitation of closely related DNA or RNA sequences.

Methods which may also be used to quantitate the expression of KERT include radio-labeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA-like format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding KERT may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) In: Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding KERT on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, KERT, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between KERT and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with KERT, or fragments thereof, and washed. Bound KERT is then detected by methods well known in the art. Purified KERT can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding KERT specifically compete with a test compound for binding KERT. In this manner, antibodies can be used to detect the presence of any peptide which shares one or more antigenic determinants with KERT.

In additional embodiments, the nucleotide sequences which encode KERT may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction
PANCTUT02

The PANCTUT02 cDNA library was constructed from cancerous pancreatic tissue obtained from a 45-year-old Caucasian female during a radical pancreaticoduodenectomy. Pathology indicated a grade 4 anaplastic carcinoma at the head of pancreas. The frozen tissue was homogenized and lysed using a POLYTRON homogenizer (PT-3000, Brinkmann Instruments, Westbury, N.Y.) in guanidinium isothiocyanate solution. The lysate was centrifuged over a 5.7M CsCl cushion using an SW28 rotor in a L8-70M ultracentrifuge (Beckman Coulter, Fullerton Calif.) for 18 hours at 25,000 rpm at ambient temperature. The RNA was extracted with acid phenol, pH 4.7, precipitated using 0.3M sodium acetate and 2.5 volumes of ethanol, resuspended in RNAse-free water, and treated with DNAse at 37° C. The RNA was extracted and precipitated as before. The mRNA was isolated with the OLIGOTEX kit (Qiagen, Chatsworth, Calif.) and used to construct the cDNA library.

The mRNA was handled according to the recommended protocols in SUPERSCRIPT Plasmid system (Life Technologies). The cDNAs were fractionated on a SEPHAROSE CL4B column (Amersham Pharmacia Biotech), and those cDNAs exceeding 400 bp were ligated into pINCY plasmid (Incyte Pharmaceuticals, Palo Alto, Calif.). The plasmid pINCY was subsequently transformed into DH5α competent cells (Life Technologies).
KERANOT02

The KERANOT02 cDNA library was constructed from a normal epidermal keratinocyte (NHEK) primary cell line acquired from Clonetics (San Diego Calif.; catalog #CC-2501), obtained from a 30-year-old black female undergoing breast reduction surgery. The frozen tissue was homogenized and lysed using a POLYTRON homogenizer (Brinkmann Instruments) in guanidinium isothiocyanate solution. The lysate was centrifuged over a 5.7M CsCl cushion using an SW28 rotor in a L8-70M ultracentrifuge (BeckmanCoulter) for 18 hours at 25,000 rpm at ambient temperature. The RNA was extracted with phenol, pH 8, precipitated using 0.3M sodium acetate and 2.5 volumes of ethanol, resuspended in RNAse-free water, and treated with DNAse at 37° C. The RNA was extracted and precipitated as before. The mRNA was isolated with the OLIGOTEX kit (Qiagen) and used to construct the cDNA library.

The mRNA was handled according to the recommended protocols in SUPERSCRIPT Plasmid system (Life Technologies). The cDNAs were fractionated on a SEPHAROSE CL4B column (Amersham Pharmacia Biotech), and those cDNAs exceeding 400 bp were ligated into pSPORT1 plasmid (Life Technolgies). The plasmid pSPORT1 was subsequently transformed into DH5α competent cells (Life Technolgies).
RSTNOT07

The BRSTNOT07 cDNA library was constructed from microscopically normal breast tissue removed from a 43-year-old Caucasian female during unilateral extended simple mastectomy following diagnosis of invasive grade 4, nuclear grade 3 mammary adenocarcinoma with extensive comedo necrosis. The frozen tissue was homogenized and lysed using a POLYTRON homogenizer (Brinkmann Instruments) in guanidinium isothiocyanate solution. The lysate was centrifuged over a 5.7M CsCl cushion using an SW28 rotor in a L8-70M ultracentrifuge (BeckmanCoulter) for 18 hours at 25,000 rpm at ambient temperature. The RNA was extracted with acid phenol, pH 4.0, precipitated using 0.3M sodium acetate and 2.5 volumes of ethanol, resuspended in RNAse-free water, and treated with DNAse at 37° C. The RNA was extracted and precipitated as before. The mRNA was isolated with the OLIGOTEX kit (Qiagen) and used to construct the cDNA library.

The mRNA was handled according to the recommended protocols in SUPERSCRIPT Plasmid system (Life Technologies). The cDNAs were fractionated on a SEPHAROSE CL4B column (Amersham Pharmacia Biotech), and those cDNAs exceeding 400 bp were ligated into pINCY plasmid (Incyte Pharmaceuticals). The plasmid pINCY was subsequently transformed into DH5a competent cells (Life Technologies).

II. Isolation and Sequencing of cDNA Clones

Plasmid DNA was released from the cells and purified using the REAL PREP 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger and Coulson (1975, J. Mol. Biol. 94:441f), using a MICROLAB 2200 (Hamilton) in combination with DNA ENGINE thermal cyclers (MJ Research) and ABI PRISM 377 DNA sequencing systems; and the reading frame was determined.
III. Similarity Searching of cDNA Clones and Their Deduced Proteins The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity.

Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam). Deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. And Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm (Attwood, T. K. et al. (1997) J. Chem. Inf. Comput. Sci. 37:417–424). PRINTS is based on non-redundant sequences obtained from sources such as SWISS-PROT, GenBank, PIR, and NRL-3D. The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1 % false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding KERT occurs. Abundance and percent abundance are also reported. Abundance directly reflects the number of times a particular transcript is represented in a cDNA library, and percent abundance is abundance divided by the total number of sequences examined in the cDNA library.

V. Extension of KERT Encoding Polynucleotides

The nucleic acid sequences of Incyte Clones 1467090, 2029060, and 2124178 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. PCR was performed using the DNA ENGINE thermal cycler (MJ Research), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK kit (Qiagen), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:4, SEQ ID NO:4. and SEQ ID NO:6 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:4, SEQ ID NO:5, and SEQ ID NO:6 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (AmershamPharmacia Biotech), and T4 polynucleotide kinase (NEN Life Science Products, Boston, Mass.). The labeled oligonucleotides are substantially purified using a SEPHADEX G-25 superfine size exclusion dextran bead column (Amersham Pharmacia Biotech). An aliquot containing 10⁷ counts per minute of the labeled probe is used in a typical membrane-based hybridization analysis of human genomic DNA digested with one of the following endonucleases: Ase I, Bgl II, Eco RI, Pst I, Xbal, or Pvu II (NEN Life Science Products).

The DNA from each digest is fractionated on a 0.7% agarose gel and transferred to nylon membranes (NYTRANPLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots for several hours, hybridization patterns are compared.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the KERT-encoding sequences, or any parts thereof, are used to detect, decrease, or inhibit expression of naturally occurring KERT. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of KERT. To inhibit transcription, a complementary oligonucleotide is designed from the most unique 5' sequence and used to prevent promoter binding to the coding sequence. To inhibit translation, a complementary oligonucleotide is designed to prevent ribosomal binding to the KERT-encoding transcript.

IX. Expression of KERT

Expression and purification of KERT is achieved using bacterial or virus-based expression systems. For expression of KERT in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express KERT upon induction with isopropyl beta-D-thiogalactopyranoside (IPTG). Expression of KERT in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding KERT by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, KERT is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham PharmaciaBiotech). Following purification, the GST moiety can s be proteolytically cleaved from KERT at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (Qiagen). Methods for protein expression and purification are discussed in Ausubel, F. M. et al. (1995 and periodic supplements) *Current Protocols in Molecular Biology*, John Wiley & Sons, New York, N.Y., ch 10, 16. Purified KERT obtained by these methods can be used directly in the following activity assay.

X. Demonstration of KERT Activity

KERT activity is demonstrated by the ability to form approximately 10 nm diameter filaments in vitro. (Steinert, P. M et al. (1976) J. Mol. Biol. 108:547–567.) KERT is dissolved at 1–2 mg/ml in buffer of 8M urea and 0.1M ammonium acetate to keep KERT in the monomeric form. The KERT solution is dialyzed against 1000 volumes of 5 mM Tris HCl (pH 7.6) and 25 mM 2-mercaptoethanol at 23° C. for 18 to 24 hours. The dialyzed KERT is diluted to about 50 μg/ml with a buffer of 5 mM Tris HCl (pH 8.0) and applied to carbon-coated grids. The grids are negative stained with 0.7% (w/v) aqueous uranyl acetate and examined by electron microscopy. The appearance of approximately 10 nm diameter filaments is a demonstration of KERT activity.

XI. Functional Assays

KERT function is assessed by expressing the sequences encoding KERT at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR 3.1 (Invitrogen, Carlsbad, Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., GFP, CD64, or a CD64-GFP fusion protein (Clontech). Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of KERT on gene expression can be assessed using highly purified populations of cells transfected with sequences encoding KERT and either CD64 or CD64-GFP. CD64 and CD64-GFP are expressed on the surface of transfected cells and bind to conserved regions of human immunoglobulin G (IgG). Transfected cells are separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding KERT and other genes of interest can be analyzed by Northern analysis or microarray techniques.

XII. Production of KERT Specific Antibodies

KERT substantially purified using polyacrylamide gel electrophoresis (PAGE) (see, e.g., Harrington, M. G. (1990) Methods Enzymol. 182:488–495), or other purification techniques, is used to immunize rabbits and to produce antibodies using standard protocols.

Alternatively, the KERT amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an ABI 43 1A Biosystems Peptide synthesizer using Fmoc-chemistry and coupled to KLH (Sigma Aldrich, St. Louis, Mo.) by reaction with N-maleimidobenzoyl-N-hydroxysuccinimide ester to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring KERT Using Specific Antibodies

Naturally occurring or recombinant KERT is substantially purified by immunoaffinity chromatography using antibodies specific for KERT. An immunoaffinity column is constructed by covalently coupling anti-KERT antibody to an activated chromatographic resin, such as CNBr-activated SEPHAROSE (Amersham Pharmacia Biotech). After the coupling, the resin is blocked and washed according to the manufacturer's instructions.

Media containing KERT are passed over the immunoaffinity column, and the column is washed under conditions that allow the preferential absorbance of KERT (e.g., high ionic strength buffers in the presence of detergent). The column is eluted under conditions that disrupt antibody/ KERT binding (e.g., a buffer of pH 2 to pH 3, or a high concentration of a chaotrope, such as urea or thiocyanate ion), and KERT is collected.

XIV. Identification of Molecules Which Interact with KERT

KERT, or biologically active fragments thereof, are labeled with $^{125}$I Bolton-Hunter reagent. (See, e.g., Bolton et al. (1973) Biochem. J. 133:529–539.) Candidate molecules previously arrayed in the wells of a multi-well plate are incubated with the labeled KERT, washed, and any wells with labeled KERT complex are assayed. Data obtained using different concentrations of KERT are used to calculate values for the number, affinity, and association of KERT with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 546 amino acids
      (B) TYPE: amino acid
      (C) STRANDEDNESS: single
      (D) TOPOLOGY: linear (vii) IMMEDIATE SOURCE:
      (A) LIBRARY: PANCTUT02
      (B) CLONE: 1467090

(xi) SEQUENCE DESCRIPTION: SEQ ID NO: 1:

```
Met Ser Arg Gln Ser Ser Val Ser Phe Arg Ser Gly Gly Ser Arg
                 5                  10                  15

Ser Phe Ser Thr Ala Ser Ala Ile Thr Pro Ser Val Ser Arg Thr
                20                  25                  30

Ser Phe Thr Ser Val Ser Arg Ser Gly Gly Gly Gly Gly Gly Gly
                35                  40                  45

Phe Gly Arg Val Ser Leu Ala Gly Ala Cys Gly Val Gly Gly Tyr
                50                  55                  60

Gly Ser Arg Ser Leu Tyr Asn Leu Gly Gly Ser Lys Arg Ile Ser
                65                  70                  75

Ile Ser Thr Ser Gly Gly Ser Phe Arg Asn Arg Phe Gly Ala Gly
                80                  85                  90

Ala Gly Gly Gly Tyr Gly Phe Gly Gly Ala Gly Ser Gly Phe
                95                 100                 105

Gly Phe Gly Gly Gly Ala Gly Gly Gly Phe Gly Leu Gly Gly Gly
               110                 115                 120

Ala Gly Phe Gly Gly Gly Phe Gly Gly Pro Gly Phe Pro Val Cys
               125                 130                 135

Pro Pro Gly Gly Ile Gln Glu Val Thr Val Asn Gln Ser Leu Leu
               140                 145                 150

Thr Pro Leu Asn Leu Gln Ile Asp Pro Ser Ile Gln Arg Val Arg
               155                 160                 165

Thr Glu Glu Arg Glu Gln Ile Lys Thr Leu Asn Asn Lys Phe Ala
               170                 175                 180

Ser Phe Ile Asp Lys Val Arg Phe Leu Glu Gln Gln Asn Lys Leu
               185                 190                 195

Leu Glu Thr Lys Trp Thr Leu Leu Gln Glu Gln Lys Ser Ala Lys
               200                 205                 210

Ser Ser Arg Leu Pro Asp Ile Phe Glu Ala Gln Ile Ala Gly Leu
               215                 220                 225

Arg Gly Gln Leu Glu Ala Leu Gln Val Asp Gly Gly Arg Leu Glu
               230                 235                 240

Ala Glu Leu Arg Ser Met Gln Asp Val Val Glu Asp Phe Lys Asn
               245                 250                 255

Lys Tyr Glu Asp Glu Ile Asn His Arg Thr Ala Ala Glu Asn Glu
               260                 265                 270

Phe Val Val Leu Lys Lys Asp Val Asp Ala Ala Tyr Met Ser Lys
               275                 280                 285
```

-continued

```
Val Glu Leu Glu Ala Lys Val Asp Ala Leu Asn Asp Glu Ile Asn
            290                 295                 300

Phe Leu Arg Thr Leu Asn Glu Thr Glu Leu Thr Glu Leu Gln Ser
            305                 310                 315

Gln Ile Ser Asp Thr Ser Val Val Leu Ser Met Asp Asn Ser Arg
            320                 325                 330

Ser Leu Asp Leu Asp Gly Ile Ile Ala Glu Val Lys Ala Gln Tyr
            335                 340                 345

Glu Glu Met Ala Lys Cys Ser Arg Ala Glu Ala Glu Ala Trp Tyr
            350                 355                 360

Gln Thr Lys Phe Glu Thr Leu Gln Ala Gln Ala Gly Lys His Gly
            365                 370                 375

Asp Asp Leu Arg Asn Thr Arg Asn Glu Ile Ser Glu Met Asn Arg
            380                 385                 390

Ala Ile Gln Arg Leu Gln Ala Glu Ile Asp Asn Ile Lys Asn Gln
            395                 400                 405

Arg Ala Lys Leu Glu Ala Ala Ile Ala Glu Ala Glu Glu Arg Gly
            410                 415                 420

Glu Leu Ala Leu Lys Asp Ala Arg Ala Lys Gln Glu Glu Leu Glu
            425                 430                 435

Ala Ala Leu Gln Arg Ala Lys Gln Asp Met Ala Arg Gln Leu Arg
            440                 445                 450

Glu Tyr Gln Glu Leu Met Ser Val Lys Leu Ala Leu Asp Ile Glu
            455                 460                 465

Ile Ala Thr Tyr Arg Lys Leu Leu Glu Gly Glu Glu Ser Arg Leu
            470                 475                 480

Ala Gly Asp Gly Val Gly Ala Val Asn Ile Ser Val Met Asn Ser
            485                 490                 495

Thr Gly Gly Ser Ser Gly Gly Gly Ile Gly Leu Thr Leu Gly
            500                 505                 510

Gly Thr Met Gly Ser Asn Ala Leu Ser Phe Ser Ser Ser Ala Gly
            515                 520                 525

Pro Gly Leu Leu Lys Ala Tyr Ser Ile Arg Thr Ala Ser Ala Ser
            530                 535                 540

Arg Arg Ser Ala Arg Asp
            545

(2) INFORMATION FOR SEQ ID NO: 2:

(i) SEQUENCE CHARACTERISTICS:
        (A) LENGTH: 551 amino acids
        (B) TYPE: amino acid
        (C) STRANDEDNESS: single
        (D) TOPOLOGY: linear (vii) IMMEDIATE SOURCE:
        (A) LIBRARY: KERANOT02
        (B) CLONE: 2029060

(xi) SEQUENCE DESCRIPTION: SEQ ID NO: 2:

Met Ser Arg Gln Ser Ser Ile Thr Phe Gln Ser Gly Ser Arg Arg
              5                  10                  15

Gly Phe Ser Thr Thr Ser Ala Ile Thr Pro Ala Ala Gly Arg Ser
             20                  25                  30

Arg Phe Ser Ser Val Ser Val Ala Arg Ser Ala Ala Gly Ser Gly
             35                  40                  45

Gly Leu Gly Arg Ile Ser Ser Ala Gly Ala Ser Phe Gly Ser Arg
```

```
                    50                  55                  60
Ser Leu Tyr Asn Leu Gly Gly Ala Lys Arg Val Ser Leu Asn Gly
                65                  70                  75
Cys Gly Ser Ser Cys Arg Ser Gly Phe Gly Arg Ala Ser Asn
                80                  85                  90
Gly Phe Gly Val Asn Ser Gly Phe Gly Tyr Gly Gly Gly Val Gly
                95                  100                 105
Gly Gly Phe Ser Gly Pro Ser Phe Pro Val Cys Pro Pro Gly Gly
                110                 115                 120
Ile Gln Glu Val Thr Val Asn Gln Ser Leu Leu Thr Pro Leu His
                125                 130                 135
Leu Gln Ile Asp Pro Thr Ile Gln Arg Val Arg Ala Glu Glu Arg
                140                 145                 150
Glu Gln Ile Lys Thr Leu Asn Asn Lys Phe Thr Ser Phe Ile Asp
                155                 160                 165
Lys Val Arg Phe Leu Glu Gln Gln Asn Lys Val Leu Glu Thr Lys
                170                 175                 180
Trp Ala Leu Leu Gln Glu Gln Gly Ser Arg Thr Val Arg Gln Asn
                185                 190                 195
Leu Glu Pro Leu Phe Asp Ser Tyr Thr Ser Glu Leu Arg Arg Gln
                200                 205                 210
Leu Glu Ser Ile Thr Thr Glu Arg Gly Arg Leu Glu Ala Glu Leu
                215                 220                 225
Arg Asn Met Gln Asp Val Val Glu Asp Phe Lys Val Arg Tyr Glu
                230                 235                 240
Asp Glu Ile Asn Lys Arg Thr Ala Ala Glu Asn Glu Phe Val Ala
                245                 250                 255
Leu Lys Lys Asp Val Asp Ala Ala Tyr Met Asn Lys Val Glu Leu
                260                 265                 270
Glu Ala Lys Val Lys Ser Leu Pro Glu Glu Ile Asn Phe Ile His
                275                 280                 285
Ser Val Phe Asp Ala Glu Leu Ser Gln Leu Gln Thr Gln Val Gly
                290                 295                 300
Asp Thr Ser Val Val Leu Ser Met Asp Asn Asn Arg Asn Leu Asp
                305                 310                 315
Leu Asp Ser Ile Ile Ala Glu Val Lys Ala Gln Tyr Glu Asp Ile
                320                 325                 330
Ala Asn Arg Ser Arg Ala Glu Ala Glu Ser Trp Tyr Gln Thr Lys
                335                 340                 345
Tyr Glu Glu Leu Gln Val Thr Ala Gly Arg His Gly Asp Asp Leu
                350                 355                 360
Arg Asn Thr Lys Gln Glu Ile Ser Glu Met Asn Arg Met Ile Gln
                365                 370                 375
Arg Leu Arg Ala Glu Ile Asp Ser Val Lys Lys Gln Cys Ser Ser
                380                 385                 390
Leu Gln Thr Ala Ile Ala Asp Ala Glu Gln Arg Gly Glu Leu Ala
                395                 400                 405
Leu Lys Asp Ala Arg Ala Lys Leu Val Asp Leu Glu Glu Ala Leu
                410                 415                 420
Gln Lys Ala Lys Gln Asp Thr Ala Arg Leu Leu Arg Glu Tyr Gln
                425                 430                 435
Glu Leu Met Asn Ile Lys Leu Ala Leu Asp Val Glu Ile Ala Thr
                440                 445                 450
```

```
Tyr Arg Lys Leu Leu Glu Gly Glu Glu Cys Arg Leu Ser Gly Glu
                455                 460                 465

Gly Val Ser Pro Val Asn Ile Ser Val Val Thr Ser Thr Leu Ser
                470                 475                 480

Ser Gly Tyr Gly Arg Gly Ser Ser Ile Gly Gly Gly Asn Leu Gly
                485                 490                 495

Leu Gly Gly Gly Ser Gly Tyr Ser Phe Thr Thr Ser Gly Gly His
                500                 505                 510

Ser Leu Gly Ala Gly Leu Gly Gly Ser Gly Phe Ser Ala Thr Ser
                515                 520                 525

Asn Arg Gly Leu Gly Gly Ser Gly Ser Ser Val Lys Phe Val Ser
                530                 535                 540

Thr Thr Ser Ser Ser Gln Lys Ser Tyr Thr His
                545                 550

(2) INFORMATION FOR SEQ ID NO: 3:

(i) SEQUENCE CHARACTERISTICS:
        (A) LENGTH: 422 amino acids
        (B) TYPE: amino acid
        (C) STRANDEDNESS: single
        (D) TOPOLOGY: linear (vii) IMMEDIATE SOURCE:
        (A) LIBRARY: BRSTNOT07
        (B) CLONE: 2124178

(xi) SEQUENCE DESCRIPTION: SEQ ID NO: 3:

Met Asn Ser Gly His Ser Phe Ser Gln Thr Pro Ser Ala Ser Phe
                  5                  10                  15

His Gly Ala Gly Gly Trp Gly Arg Pro Arg Ser Phe Pro Arg
                 20                  25                  30

Ala Pro Thr Val His Gly Gly Ala Gly Ala Arg Ile Ser Leu
                 35                  40                  45

Ser Phe Thr Thr Arg Ser Cys Pro Pro Gly Gly Ser Trp Gly
                 50                  55                  60

Ser Gly Arg Ser Ser Pro Leu Leu Gly Gly Asn Gly Lys Ala Thr
                 65                  70                  75

Met Gln Asn Leu Asn Asp Arg Leu Ala Ser Tyr Leu Glu Lys Val
                 80                  85                  90

Arg Ala Leu Glu Glu Ala Asn Met Lys Leu Glu Ser Arg Ile Leu
                 95                 100                 105

Lys Trp His Gln Gln Arg Asp Pro Gly Ser Lys Lys Asp Tyr Ser
                110                 115                 120

Gln Tyr Glu Glu Asn Ile Thr His Leu Gln Glu Gln Ile Val Asp
                125                 130                 135

Gly Lys Met Thr Asn Ala Gln Ile Ile Leu Leu Ile Asp Asn Ala
                140                 145                 150

Arg Met Ala Val Asp Asp Phe Asn Leu Lys Tyr Glu Asn Glu His
                155                 160                 165

Ser Phe Lys Lys Asp Leu Glu Ile Glu Val Glu Gly Leu Arg Arg
                170                 175                 180

Thr Leu Asp Asn Leu Thr Ile Val Thr Thr Asp Leu Glu Gln Glu
                185                 190                 195

Val Glu Gly Met Arg Lys Glu Leu Ile Leu Met Lys Lys His His
                200                 205                 210
```

-continued

```
Glu Gln Glu Met Glu Lys His His Val Pro Ser Asp Phe Asn Val
                215                 220                 225

Asn Val Lys Val Asp Thr Gly Pro Arg Glu Asp Leu Ile Lys Val
                230                 235                 240

Leu Glu Asp Met Arg Gln Glu Tyr Glu Leu Ile Ile Lys Lys Lys
                245                 250                 255

His Arg Asp Leu Asp Thr Trp Tyr Lys Glu Gln Ser Ala Ala Met
                260                 265                 270

Ser Gln Glu Ala Ala Ser Pro Ala Thr Val Gln Ser Arg Gln Gly
                275                 280                 285

Asp Ile His Glu Leu Lys Arg Thr Phe Gln Ala Leu Glu Ile Asp
                290                 295                 300

Leu Gln Thr Gln Tyr Ser Thr Lys Ser Ala Leu Glu Asn Met Leu
                305                 310                 315

Ser Glu Thr Gln Ser Arg Tyr Ser Cys Lys Leu Gln Asp Met Gln
                320                 325                 330

Glu Ile Ile Ser His Tyr Glu Glu Leu Thr Gln Leu Arg His
                335                 340                 345

Glu Leu Glu Arg Gln Asn Asn Glu Tyr Gln Val Leu Leu Gly Ile
                350                 355                 360

Lys Thr His Leu Glu Lys Glu Ile Thr Thr Tyr Arg Arg Leu Leu
                365                 370                 375

Glu Gly Glu Ser Glu Gly Thr Arg Glu Glu Ser Lys Ser Ser Met
                380                 385                 390

Lys Val Ser Ala Thr Pro Lys Ile Lys Ala Ile Thr Gln Glu Thr
                395                 400                 405

Ile Asn Gly Arg Leu Val Leu Cys Gln Val Asn Glu Ile Gln Lys
                410                 415                 420

His Ala (2) INFORMATION FOR SEQ ID NO: 4:

(i) SEQUENCE CHARACTERISTICS:
        (A) LENGTH: 1875 base pairs
        (B) TYPE: nucleic acid
        (C) STRANDEDNESS: single
        (D) TOPOLOGY: linear (vii) IMMEDIATE SOURCE:
        (A) LIBRARY: PANCTUT02
        (B) CLONE: 1467090

(xi) SEQUENCE DESCRIPTION: SEQ ID NO: 4 :

CTTCTGCGTC CTGCTGAGCT CTGTTCTCTC CAGCACCTCC CAACCCACTA GTGCCTGGTT      60

CTCTTGCTCC ACCAGGAACA AGCCACCATG TCTCGCCAGT CAAGTGTGTC CTTCCGGAGC     120

GGGGGCAGTC GTAGCTTCAG CACCGCCTCT GCCATCACCC CGTCTGTCTC CCGCACCAGC     180

TTCACCTCCG TGTCCCGGTC CGGGGGTGGC GGTGGTGGTG GCTTCGGCAG GGTCAGCCTT     240

GCGGGTGCTT GTGGAGTGGG TGGCTATGGC AGCCGGAGCC TCTACAACCT GGGGGGCTCC     300

AAGAGGATAT CCATCAGCAC TAGTGGTGGC AGCTTCAGGA ACCGGTTTGG TGCTGGTGCT     360

GGAGGCGGCT ATGGCTTTGG AGGTGGTGCC GGTAGTGGAT TTGGTTTCGG CGGTGGAGCT     420

GGTGGTGGCT TTGGGCTCGG TGGCGGAGCT GGCTTTGGAG GTGGCTTCGG TGGCCCTGGC     480

TTTCCTGTCT GCCCTCCTGG AGGTATCCAA GAGGTCACTG TCAACCAGAG TCTCCTGACT     540

CCCCTCAACC TGCAAATCGA CCCCAGCATC CAGAGGGTGA GGACCGAGGA GCGCGAGCAG     600
```

```
ATCAAGACCC TCAACAATAA GTTTGCCTCC TTCATCGACA AGGTGCGGTT TCTGGAGCAG    660

CAGAACAAGC TGCTGGAGAC CAAGTGGACG CTGCTGCAGG AGCAGAAGTC GGCCAAGAGC    720

AGCCGCCTCC CAGACATCTT TGAGGCCCAG ATTGCTGGCC TTCGGGGTCA GCTTGAGGCA    780

CTGCAGGTGG ATGGGGCCG CCTGGAGGCG GAGCTGCGGA GCATGCAGGA TGTGGTGGAG     840

GACTTCAAGA ATAAGTACGA AGATGAAATT AACCACCGCA CAGCTGCTGA GAATGAGTTT    900

GTGGTGCTGA AGAAGGATGT GGATGCTGCC TACATGAGCA AGGTGGAGCT GGAGGCCAAG    960

GTGGATGCCC TGAATGATGA GATCAACTTC CTCAGGACCC TCAATGAGAC GGAGTTGACA   1020

GAGCTGCAGT CCCAGATCTC CGACACATCT GTGGTGCTGT CCATGGACAA CAGTCGCTCC   1080

CTGGACCTGG ACGGCATCAT CGCTGAGGTC AAGGCGCAGT ATGAGGAGAT GGCCAAATGC   1140

AGCCGGGCTG AGGCTGAAGC CTGGTACCAG ACCAAGTTTG AGACCCTCCA GGCCCAGGCT   1200

GGGAAGCATG GGGACGACCT CCGGAATACC CGGAATGAGA TTTCAGAGAT GAACCGGGCC   1260

ATCCAGAGGC TGCAGGCTGA GATCGACAAC ATCAAGAACC AGCGTGCCAA GTTGGAGGCC   1320

GCCATTGCCG AGGCTGAGGA GCGTGGGGAG CTGGCGCTCA AGGATGCTCG TGCCAAGCAG   1380

GAGGAGCTGG AAGCCGCCCT GCAGCGGGCC AAGCAGGATA TGGCACGGCA GCTGCGTGAG   1440

TACCAGGAAC TCATGAGCGT GAAGCTGGCC CTGGACATCG AGATCGCCAC CTACCGCAAG   1500

CTGCTGGAGG GCGAGGAGAG CCGGTTGGCT GGAGATGGAG TGGGAGCCGT GAATATCTCT   1560

GTGATGAATT CCACTGGTGG CAGTAGCAGT GGCGGTGGCA TTGGGCTGAC CCTCGGGGA    1620

ACCATGGGCA GCAATGCCCT GAGCTTCTCC AGCAGTGCGG GTCCTGGGCT CCTGAAGGCT   1680

TATTCCATCC GGACCGCATC CGCCAGTCGC AGGAGTGCCC GCGACTGAGC CGCCTCCCAC   1740

CACTCCACTC CTCCAGCCAC CACCCACAAT CACAAGAAGA TTCCCACCCC TGCCTCCCAT   1800

GCCTGGTCCC AAGACAGTGA GACAGTCTGG AAAGTGATGT CAGAATAGCT TCCAATAAAG   1860

CACCTCATTC TGAGC                                                    1875

(2) INFORMATION FOR SEQ ID NO: 5:

(i) SEQUENCE CHARACTERISTICS:
        (A) LENGTH: 2167 base pairs
        (B) TYPE: nucleic acid
        (C) STRANDEDNESS: single
        (D) TOPOLOGY: linear (vii) IMMEDIATE SOURCE:
        (A) LIBRARY: KERANOT02
        (B) CLONE: 2029060

(xi) SEQUENCE DESCRIPTION: SEQ ID NO: 5 :

CTGCCTGTAC CAGCCCACCT CAGGTGCCTT CTCGCCGGCC TTCCTCACCC ACCATGTCTC     60

GGCAGTCCTC CATCACCTTC CAGTCTGGCA GCCGCAGGGG CTTCAGCACC ACCTCGGCCA    120

TCACCCCGGC AGCTGGCCGC TCCCGCTTCA GCTCTGTCTC TGTGGCCCGC TCTGCAGCAG    180

GGAGTGGGGG CCTGGGAAGG ATCAGCAGTG CTGGGGCCAG CTTTGGAAGC CGCAGCCTCT    240

ACAACCTGGG GGGTGCCAAG CGGGTCTCCC TCAATGGGTG TGGCAGCAGC TGCCGAAGTG    300

GCTTTGGTGG CAGGGCCAGC AACGGGTTTG GAGTCAACAG TGGATTTGGC TATGGAGGTG    360

GAGTTGGAGG AGGCTTCAGT GGCCCCAGCT TCCCCGTGTG TCCCCCTGGA GGCATCCAAG    420

AGGTCACTGT CAACCAGAGT CTCCTGACTC CTCTTCACCT GCAAATCGAC CCCACCATCC    480

AGCGGGTGCG GGCCGAGGAG CGCGAGCAGA TCAAGACCCT CAACAATAAG TTCACCTCCT    540

TCATCGACAA GGTGAGGTTC TTGGAGCAGC AGAACAAGGT CCTGGAGACC AAGTGGGCCC    600
```

-continued

| | |
|---|---|
| TCCTGCAGGA GCAGGGCTCC AGGACTGTGA GGCAGAACCT AGAGCCCCTC TTTGATTCCT | 660 |
| ATACCAGTGA GCTCCGACGG CAGCTGGAAA GCATCACCAC CGAGAGGGGC AGGCTTGAAG | 720 |
| CTGAACTGAG GAACATGCAG GATGTTGTGG AAGATTTCAA AGTCAGGTAC GAAGATGAAA | 780 |
| TTAACAAGCG CACAGCTGCT GAGAATGAAT TTGTAGCCCT GAAAAAGGAC GTAGATGCTG | 840 |
| CCTATATGAA CAAGGTGGAG CTGGAAGCCA AGGTCAAATC TCTGCCTGAG GAGATCAACT | 900 |
| TCATCCACTC AGTCTTTGAT GCAGAGCTGT CCCAGTTGCA GACCCAGGTC GGTGACACAT | 960 |
| CCGTGGTGCT GTCCATGGAC AACAACCGCA ACCTGGACCT GGATAGTATC ATCGCCGAGG | 1020 |
| TCAAAGCACA ATACGAGGAC ATTGCCAACC GCAGCCGGGC CGAGGCTGAG TCCTGGTACC | 1080 |
| AGACCAAGTA CGAGGAGCTG CAGGTCACCG CAGGCAGACA TGGGGATGAC CTTCGAAACA | 1140 |
| CCAAACAAGA GATCTCTGAA ATGAACCGCA TGATCCAGAG GCTGAGAGCT GAGATTGACA | 1200 |
| GCGTCAAGAA GCAGTGTTCC AGCTTGCAAA CGGCCATTGC TGATGCAGAG CAGCGGGGAG | 1260 |
| AACTGGCTCT CAAGGATGCA CGGGCCAAGC TGGTGGACCT TGAGGAGGCC CTGCAGAAGG | 1320 |
| CCAAGCAGGA CACGGCTCGG CTCCTGCGTG AGTACCAGGA GCTGATGAAC ATCAAGCTGG | 1380 |
| CCCTGGACGT GGAGATCGCC ACCTACCGCA AGCTGCTGGA AGGCGAGGAG TGCAGGTTGA | 1440 |
| GTGGAGAGGG AGTTTCTCCA GTTAACATTT CTGTGGTCAC CTCTACTCTT TCCAGTGGCT | 1500 |
| ATGGACGCGG CAGCAGCATT GGAGGTGGAA ACCTGGGCCT CGGTGGGGGC AGCGGCTACT | 1560 |
| CCTTCACCAC CAGTGGTGGG CATAGCCTGG GTGCAGGCCT GGGAGGTTCT GGATTCAGTG | 1620 |
| CCACCAGCAA CCGGGGCTTA GGGGGCAGTG GTTCTAGCGT CAAGTTTGTC TCCACCACAT | 1680 |
| CCTCCAGCCA GAAGAGCTAC ACGCACTAAG AGAGCCCCAT GGCTCCCTCT ACCCTGCCTT | 1740 |
| GAGGCCTGTT TGCAGTCACA CCTGGACACC AGGGTCCTCC TCCTTCCTCT CTCCTTGTAA | 1800 |
| GGTGCACCTG TGCTGCTGGG AGCCTGGAGT ACTGGCTATA CCCATTCCCA GGCCTAAGCC | 1860 |
| AGCCTCTCCC TCCTGACAGT GCCCAGACTG CCAGCAGCAC CCGTCTGTTA CACATGTGAA | 1920 |
| ACCAAAGCCT GCTCTCTCCT AAGGCTCTCA TTCAGCCTAT CTTGCGAGGC CCGGGCAGCT | 1980 |
| GGAAAGTCCT CCTCCAGCTC CACCTCCCTC CCTCCCTCCA GATGCAGAGG CTGGGGAGTC | 2040 |
| TCTCAATGCC AGGTTGTCAC CCACCTGTCT CATAGTGTTT ATAAGTGGCC TGCTGGGAGT | 2100 |
| GAGTGCTCCC TCTGTTCCCT CCCTGGAATG TGTCTATTAA ATGCATGTGT CACCTGAAAA | 2160 |
| AAAAAAA | 2167 |

(2) INFORMATION FOR SEQ ID NO: 6:

(i) SEQUENCE CHARACTERISTICS:
        (A) LENGTH: 1623 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT07
        (B) CLONE: 2124178

(xi) SEQUENCE DESCRIPTION: SEQ ID NO: 6:

| | |
|---|---|
| CGGTGCCAGG GAGTGGAGCA GAGCTCAGCC CCGTCCCAAA CACAGATGGG ACCATGAACT | 60 |
| CCGGACACAG CTTCAGCCAG ACCCCCTCGG CCTCCTTCCA TGGCGCCGGA GGTGGCTGGG | 120 |
| GCCGGCCCAG GAGCTTCCCC AGGGCTCCCA CCGTCCATGG CGGTGCGGGG GGAGCCCGCA | 180 |
| TCTCCCTGTC CTTCACCACG CGGAGCTGCC CACCCCCTGG AGGGTCTTGG GGTTCTGGAA | 240 |
| GAAGCAGCCC CCTACTAGGC GGAAATGGGA AGGCCACCAT GCAGAATCTC AACGACCGCC | 300 |

-continued

```
TGGCCTCCTA CCTGGAGAAG GTTCGCGCCC TGGAGGAGGC CAACATGAAG CTGGAAAGCC      360
GCATCCTGAA ATGGCACCAG CAGAGAGATC CTGGCAGTAA GAAAGATTAT TCCCAGTATG      420
AGGAAAACAT CACACACCTG CAGGAGCAGA TAGTGGATGG TAAGATGACC AATGCTCAGA      480
TTATTCTTCT CATTGACAAT GCCAGGATGG CAGTGGATGA CTTCAACCTC AAGTATGAAA      540
ATGAACACTC CTTTAAGAAA GACTTGGAAA TTGAAGTCGA GGGCCTCCGA AGGACCTTAG      600
ACAACCTGAC CATTGTCACA ACAGACCTAG AACAGGAGGT GGAAGGAATG AGGAAAGAGC      660
TCATTCTCAT GAAGAAGCAC CATGAGCAGG AAATGGAGAA GCATCATGTG CCAAGTGACT      720
TCAATGTCAA TGTGAAGGTG GATACAGGTC CCAGGGAAGA TCTGATTAAG GTCCTGGAGG      780
ATATGAGACA AGAATATGAG CTTATAATAA AGAAGAAGCA TCGAGACTTG GACACTTGGT      840
ATAAAGAACA GTCTGCAGCC ATGTCCCAGG AGGCAGCCAG TCCAGCCACT GTGCAGAGCA      900
GACAAGGTGA CATCCACGAA CTGAAGCGCA CATTCCAGGC CCTGGAGATT GACCTGCAGA      960
CACAGTACAG CACGAAATCT GCTTTGGAAA ACATGTTATC CGAGACCCAG TCTCGGTACT     1020
CCTGCAAGCT CCAGGACATG CAAGAGATCA TCTCCCACTA TGAGGAGGAA CTGACGCAGC     1080
TACGCCATGA ACTGGAGCGG CAGAACAATG AATACCAAGT GCTGCTGGGC ATCAAAACCC     1140
ACCTGGAGAA GGAAATCACC ACGTACCGAC GGCTCCTGGA GGGAGAGAGT GAAGGGACAC     1200
GGGAAGAATC AAAGTCGAGC ATGAAAGTGT CTGCAACTCC AAAGATCAAG GCCATAACCC     1260
AGGAGACCAT CAACGGAAGA TTAGTTCTTT GTCAAGTGAA TGAAATCCAA AAGCACGCAT     1320
GAGACCAATG AAAGTTTCCG CCTGTTGTAA AATCTATTTT CCCCCAAGGA AAGTCCTTGC     1380
ACAGACACCA GTGAGTGAGT TCTAAAAGAT ACCCTTGGAA TTATCAGACT CAGAAACTTT     1440
TATTTTTTTT TTCTGTAACA GTCTCACCAG ACTTCTCATA ATGCTCTTAA TATATTGCAC     1500
TTTTCTAATC AAAGTGCGAG TTTATGAGGG TAAAGCTCTA CTTTCCTACT GCAGCCTTCA     1560
GATTCTCATC ATTTTGCATC TATTTTGTAG CCAATAAAAC TCCGCACTAG CAAAAAAAAA     1620
AAA                                                                 1623
```

What is claimed is:

1. A substantially purified polypeptide comprising an amino acid sequence selected from the group consisting of SEQ ID NO:1, SEQ ID NO:2 and SEQ ID NO:3.

2. A substantially purified variant having at least 90% amino acid identity to the amino acid sequence of claim 1 wherein said variants are able to form approximately 10 nm diameter filaments in vitro.

3. A composition comprising the polypeptide of claim 1 in conjunction with a suitable carrier.

4. A method for using a protein to screen a library of molecules and compounds to identify a molecule or compound which specifically binds the protein, the method comprising:

(a) contacting the protein of claim 1 with a library of molecules or compounds under conditions that allow specific binding; and (b) detecting specific binding, thereby identifying a molecule or compound which specifically binds the protein.

5. The method of claim 4 wherein the library is selected from peptides or proteins, agonists, antagonists, antibodies, immunoglobulins, inhibitors, drug compounds and pharmaceutical agents.

* * * * *